(12) United States Patent
Peeters

(10) Patent No.: US 9,041,538 B2
(45) Date of Patent: May 26, 2015

(54) DIAGNOSTIC RADIO FREQUENCY IDENTIFICATION SENSORS AND APPLICATIONS THEREOF

(75) Inventor: John P. Peeters, Williamsburg, VA (US)

(73) Assignee: Altivera, LLC, Potomac, MD (US)

( * ) Notice: Subject to any disclaimer, the term of this patent is extended or adjusted under 35 U.S.C. 154(b) by 523 days.

(21) Appl. No.: 13/108,643

(22) Filed: May 16, 2011

(65) Prior Publication Data

US 2011/0217205 A1     Sep. 8, 2011

Related U.S. Application Data

(62) Division of application No. 10/530,901, filed as application No. PCT/US2005/002171 on Jan. 24, 2005, now Pat. No. 7,969,307.

(60) Provisional application No. 60/539,419, filed on Jan. 27, 2004.

(51) Int. Cl.
*G01N 33/53*     (2006.01)
*G01N 35/00*     (2006.01)
(Continued)

(52) U.S. Cl.
CPC ........ *G01N 35/00871* (2013.01); *A61B 5/0002* (2013.01); *A61B 5/0008* (2013.01); *A61B 5/02* (2013.01); *A61B 5/1112* (2013.01); *A61B 5/1411* (2013.01); *A61B 5/14532* (2013.01); *A61B 5/14546* (2013.01); *A61B 5/1491* (2013.01); *A61B 5/411* (2013.01); *A61B 5/4839* (2013.01); *A61B 2560/0242* (2013.01); *A61B 2560/0412* (2013.01); *A61B 2560/0462* (2013.01); *A61B 2562/08* (2013.01); *A62B 99/00* (2013.01); *G01D 21/00* (2013.01); *G01K 13/00* (2013.01); *G01N 33/54373* (2013.01); *G01N 33/5438* (2013.01); *G01N 33/58* (2013.01); *G01N 2035/00881* (2013.01); *G06K 19/0717* (2013.01); *G08B 31/00* (2013.01); *H04M 1/7253* (2013.01); *H04M 2250/02* (2013.01);
(Continued)

(58) Field of Classification Search
CPC ............... A61B 2560/0242; A61B 2560/0285; A61B 2560/0412; A61B 5/02; A61B 5/14532; A61B 5/14546
See application file for complete search history.

(56) References Cited

U.S. PATENT DOCUMENTS 3,253,588 A    5/1966    Vuilleumier et al.
5,634,468 A    6/1997    Platt et al.
(Continued)

*Primary Examiner* — Benjamin C Lee
*Assistant Examiner* — Rajsheed Black-Childress
(74) *Attorney, Agent, or Firm* — Dickinson Wright LLC

(57) ABSTRACT

An integrated passive wireless chip diagnostic sensor system is described that can be interrogated remotely with a wireless device such as a modified cell phone incorporating multi-protocol RFID reader capabilities (such as the emerging Gen-2 standard) or Bluetooth, providing universal easy to use, low cost and immediate quantitative analyses, geolocation and sensor networking capabilities to users of the technology. The present invention can be integrated into various diagnostic platforms and is applicable for use with low power sensors such as thin films, MEMS, electrochemical, thermal, resistive, nano or microfluidic sensor technologies. Applications of the present invention include on-the-spot medical and self-diagnostics on smart skin patches, Point-of-Care (POC) analyses, food diagnostics, pathogen detection, disease-specific wireless biomarker detection, remote structural stresses detection and sensor networks for industrial or Homeland Security using low cost wireless devices such as modified cell phones.

13 Claims, 23 Drawing Sheets

(51) Int. Cl.

| | | |
|---|---|---|
| A61B 5/00 | (2006.01) | |
| A61B 5/11 | (2006.01) | |
| A62B 99/00 | (2009.01) | |
| G01D 21/00 | (2006.01) | |
| G01K 13/00 | (2006.01) | |
| G01N 33/543 | (2006.01) | |
| G01N 33/58 | (2006.01) | |
| G06K 19/07 | (2006.01) | |
| G08B 31/00 | (2006.01) | |
| A61B 5/02 | (2006.01) | |
| A61B 5/15 | (2006.01) | |
| A61B 5/145 | (2006.01) | |
| A61B 5/1491 | (2006.01) | |
| H04M 1/725 | (2006.01) | |
| H04W 64/00 | (2009.01) | |
| H04W 80/00 | (2009.01) | |
| H04W 84/18 | (2009.01) | |
| H04W 88/02 | (2009.01) | |
| H04W 88/06 | (2009.01) | |

(52) U.S. Cl.
CPC ............... *H04W64/00* (2013.01); *H04W 80/00* (2013.01); *H04W 84/18* (2013.01); *H04W 88/02* (2013.01); *H04W 88/06* (2013.01); A61B 5/14514 (2013.01); *A61B 5/6832* (2013.01); *A61B 2560/0285* (2013.01); G06K 19/0723 (2013.01)

(56) References Cited

U.S. PATENT DOCUMENTS

| | | | |
|---|---|---|---|
| 5,774,062 A | 6/1998 | Ikefuji | |
| 6,166,626 A | 12/2000 | Janky et al. | |
| 6,172,609 B1 | 1/2001 | Lu et al. | |
| 6,285,899 B1 | 9/2001 | Ghaem et al. | |
| 6,287,252 B1 | 9/2001 | Lugo | |
| 6,297,727 B1 | 10/2001 | Nelson, Jr. | |
| 6,315,719 B1 | 11/2001 | Rode et al. | |
| 6,428,475 B1 | 8/2002 | Shen | |
| 6,583,722 B2 | 6/2003 | Jeutter et al. | |
| 6,615,074 B2 | 9/2003 | Mickle et al. | |
| 6,686,843 B2 | 2/2004 | Felkowitz | |
| 6,937,154 B2 | 8/2005 | Zeps et al. | |
| 7,023,341 B2 | 4/2006 | Stilp | |
| 7,026,941 B1 | 4/2006 | Anderson | |
| 7,034,683 B2 | 4/2006 | Ghazarian | |
| 7,142,114 B2 | 11/2006 | Crowley | |
| 7,148,803 B2 | 12/2006 | Bandy et al. | |
| 7,178,416 B2 * | 2/2007 | Whelan et al. | 73/864.91 |
| 7,652,188 B2 | 1/2010 | Levanon et al. | |
| 8,636,648 B2 * | 1/2014 | Gazdzinski | 600/109 |
| 2002/0099634 A1 * | 7/2002 | Coutts et al. | 705/35 |
| 2002/0126057 A1 * | 9/2002 | King et al. | 343/725 |
| 2002/0175818 A1 * | 11/2002 | King et al. | 340/572.8 |
| 2002/0180605 A1 | 12/2002 | Ozguz et al. | |
| 2003/0173408 A1 * | 9/2003 | Mosher et al. | 235/492 |
| 2003/0187338 A1 | 10/2003 | Say et al. | |
| 2004/0029109 A1 * | 2/2004 | Lai | 435/5 |
| 2004/0100376 A1 | 5/2004 | Lye et al. | |
| 2004/0225199 A1 | 11/2004 | Evanyk et al. | |
| 2004/0233043 A1 * | 11/2004 | Yazawa et al. | 340/10.3 |
| 2005/0009122 A1 * | 1/2005 | Whelan et al. | 435/7.32 |
| 2005/0022581 A1 * | 2/2005 | Sunshine | 73/31.05 |
| 2005/0101843 A1 | 5/2005 | Quinn et al. | |
| 2008/0197975 A1 * | 8/2008 | Ryoo et al. | 340/10.1 |
| 2009/0209904 A1 | 8/2009 | Peeters | |

* cited by examiner

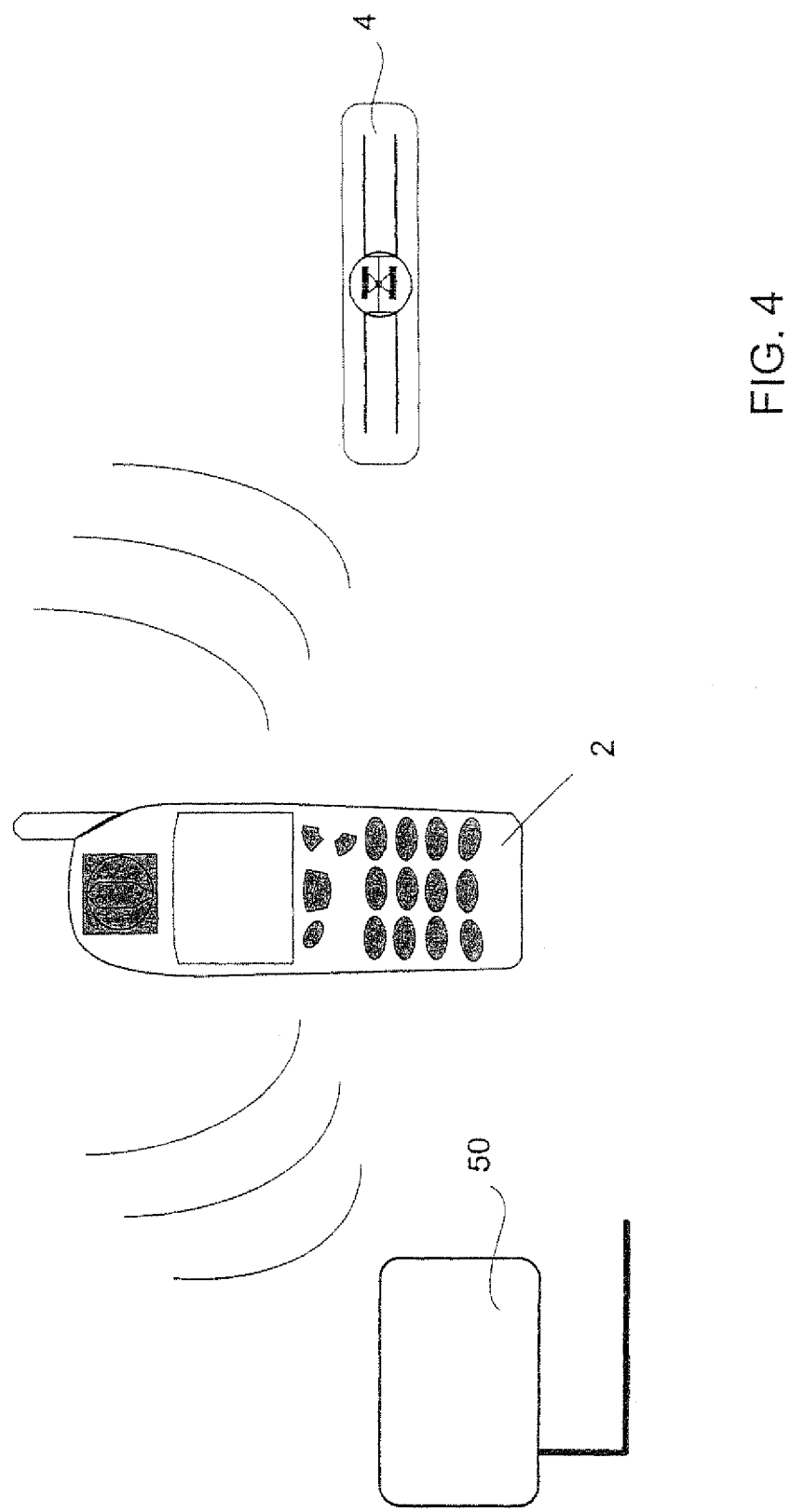

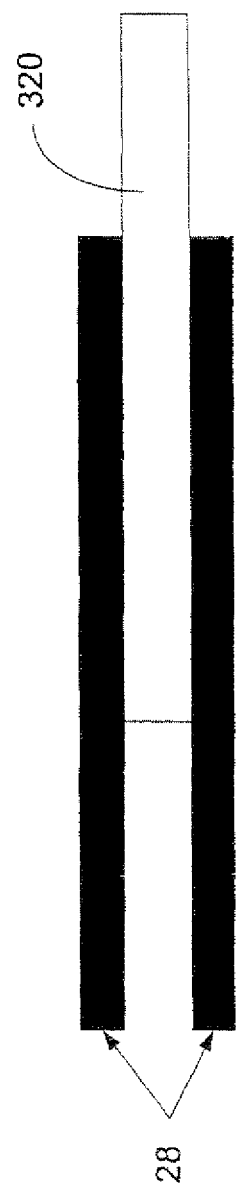
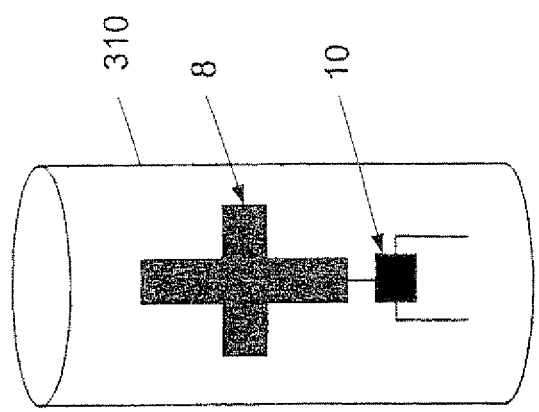
FIG. 19 A
FIG. 19 B

DIAGNOSTIC RADIO FREQUENCY IDENTIFICATION SENSORS AND APPLICATIONS THEREOF

CROSS REFERENCE TO RELATED APPLICATIONS

This is a divisional application which claims priority to U.S. patent application Ser. No. 10/530,901, filed Apr. 8, 2005 now U.S. Pat. No. 7,969,307, entitled "Diagnostic Radio Frequency Identification Sensors And Applications Thereof" which claims priority to PCT Application No. PCT/US05/02171, filed Jan. 24, 2005 which claims priority to U.S. Provisional Application 60/539,419, filed on Jan. 27, 2004, all of which are incorporated herein by reference in their entirety.

TECHNICAL FIELD

The present invention generally relates to radio frequency identification (RFID) tags, and more specifically to a system having RFID tags that include diagnostic sensors, wherein the RFID tag and sensor are accessible by a wireless device such as a modified cell phone with a multi-protocol reader capability.

BACKGROUND

The conventional radio frequency identification (RFID) tag systems include an RFID tag that transmits data for reception by an RFID reader (also referred to as an interrogater). In a typical RFID system, individual objects (e.g., store merchandise) are equipped with a relatively small tag that contains a transponder. The transponder has a memory chip that is given a unique electronic product code. The RFID reader emits a signal activating the transponder within the tag through the use of a communication protocol. Accordingly, the RFID reader is capable of reading and writing data to the tag. Additionally, the RFID tag reader processes the data according to the RFID tag system application. Currently, there are passive and active type RFID tags. The passive type RFID tag does not contain an internal power source, but is powered by radio frequency signals received from the RFID reader. Alternatively, the active type RFID tag contains an internal power source that enables the active type RFID tag to possess greater transmission ranges and memory capacity. The use of a passive versus an active tag is dependent upon the particular application.

Accordingly, RFID tag systems have found use in a variety of applications. RFID tag system applications include animal identification, beer keg tracking, and automobile key-and-lock, anti-theft systems. Although the conventional RFID tag systems have been used in a variety of applications, the conventional systems have several disadvantages.

A first disadvantage includes the inability of a RFID reader to communicate through the use of multiple protocols. In particular, the conventional RFID reader is capable of reading only those RFID tags that the RFID reader is programmed to read. That is, the RFID reader is adapted to communicate only through the use of a preprogrammed protocol. Consequently, the conventional RFID readers are incapable of automatically updating or changing protocols. Thus, the current RFID readers are unable to communicate with RFID tags having a communication protocol that differs from the RFID reader pre-programmed protocol. A second disadvantage includes the inability to conveniently monitor objects containing the RFID tag from virtually any location. A third disadvantage of conventional RFID tag systems is the inability of wireless devices, such as cellular telephones and personal digital assistants (PDAs), to be used as RFID readers/interrogaters. The ability to interrogate RFID tags with conventional wireless devices would provide a convenient method of accessing and/or analyzing data obtained through the use of the RFID tag. Yet another disadvantage is that conventional RFID tag systems are incapable of cost effective, efficient and convenient monitoring of the physical, biological, and chemical characteristics of a person. For example, the conventional systems do not enable the detection of given biomarkers, pathogens, chemicals or other hazards, near or experienced by a person.

The embodiments described herein were developed in light of these and other disadvantages of known RFID tag systems.

BRIEF SUMMARY

This invention is directed to a system and method for low cost wireless diagnostics using modified radio frequency identification (RFID) tags that are combined with novel types of diagnostic sensors. A further aspect of this invention is that the diagnostic sensors can be read and analyzed on the spot by low cost wireless devices such as modified cell phones that incorporate multi-protocol RFID reader and communication standards such as Gen-2. The technology allows a modified cell phone to be used to directly identify external threats or to perform almost any type of diagnostic test on a single platform using low cost disposable passive RFID-sensors. The reader capabilities of a modified personal wireless device may also include other reader protocols such as Bluetooth, Zigbee or IEEE 1073 and read virtually any type of active or passive sensors, resulting in a new class of wireless readers that are truly universal and flexible to control virtually any application or provide a means for analyzing any type of sensor, including diagnostic sensors.

Accordingly, a diagnostics system is disclosed that includes a flexible patch having an adhesive portion that is adapted to be positioned on a surface. A radio frequency identification (RFID) tag and sensor module is integrated with the patch. The RFID tag and sensor module includes at least one antenna, an RFID electronic chip, and at least one sensor. The RFID tag may be either passive or active. Furthermore the technology described here does not need to be limited to RFID and may also be applied to other wireless interrogation protocols and chip technologies such as Bluetooth, Zigbee or other emerging technologies. For the sake of clarity RFID is used in this patent application but it is understood that RFID, Bluetooth, Zigbee or other similar technologies may be used interchangeably.

The RFID tag and sensor module responds to a stimulus by wirelessly transmitting and receiving, through the use of the antenna, signals that correspond to the stimulus. A wireless RFID reader is included that is adapted to communicate, through the use of multiple protocols, with the RFID tag and sensor module. Additionally, the RFID reader is adapted to read and analyze virtually any RFID tag and sensor module. As such, the RFID reader is adapted to retrieve the electronic identification of a tag and sensor module and download software that enables reading and analyses of the tag and sensor from a database. The RFID reader is also capable of communicating over a network through the use of multiple communication protocols. In one embodiment, the RFID reader is a cellular telephone. The diagnostics system may also include a remote storage/data access unit that remotely stores data transmitted and/or received by the RFID tag and sensor module and the RFID reader. A remote wireless device is also disclosed that enables access to the RFID tag and sensor module, the RFID reader, and the remote storage/data access unit from virtually any location.

Additionally, a method of transmitting and remotely analyzing data from a RFID tag and sensor module is disclosed. The method includes the step of activating the RFID tag and sensor module through the use of a wireless RFID reader. A second step includes receiving data from the RFID tag and sensor module, wherein the data includes RFID tag identification information. An additional step includes transmitting the received data to an external remote storage/data processing unit through the use of a network. Yet another step includes processing the data through the use of the remote storage/data processing unit. As indicated above, in addition to RFID technology, Bluetooth or similar technology may also be used as an alternative, whereby the cell phone is Bluetooth equipped and may power a remote RF diagnostic sensor that is Bluetooth compatible.

An immunoassay test strip for use in conducting diagnostic measurements is also disclosed. The immunoassay test strip includes a substrate and at least one test area located on the substrate for capturing antigens. Additionally, the immunoassay test strip includes a RFID tag and sensor module integrated with the substrate. The RFID tag and sensor module is adapted to sense and transmit signals that correspond to the antigens captured by the at least one test area.

Another method is disclosed for manufacturing a pathogen-specific RFID tag and sensor module. The method includes the steps of providing a substrate and printing conductive leads on the substrate, wherein the conductive leads define a sensor area. The method also includes printing a protective cap doped with a material that is sensitive to the enzymatic action within the sensor area. Furthermore, the step of printing an antenna on the substrate is included. Accordingly, the method includes the step of integrating an RFID tag and sensor module with the substrate.

An additional feature of this invention is that the wireless devices or the sensors can also be geolocated anywhere by a global positioning system (GPS) and/or non-GPS triangulation means and can be interrogated remotely through the use of the Internet or by any other wireless device that can access a cell phone reader, thereby combining electronic product code (EPC) and cellular telephone technologies into a single platform.

These and other objects, advantages and features will become readily apparent in view of the following detailed description of the invention.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

FIG. 4 is a system diagram of an RFID diagnostics system for monitoring glucose with a modified cellular telephone that is adapted to read the patch of FIG. 1.

FIGS. 19A and 19B illustrate the use of a RFID tag and sensor module for the detection of insect infestation within a structure.

DETAILED DESCRIPTION

The technology described herein allows sensor technologies to be coupled to radio frequency identification (RFID) tags that provide both the power and the wireless interface for the sensor at very low cost. Another aspect of this invention is that common wireless devices such as cell phones can be modified to include the necessary logic and components to become RFID readers. The reader device can furthermore include a multi-protocol RFID reader capability, making it a universal reader for any RFID EPC tag or RFID-sensor tag, regardless of the manufacturer. This technology combination allows on the spot sophisticated processing of complex sensor data at a relatively low cost. The technology also allows RFID tags or sensor tags to be accessed by the Internet using the wireless reader device as a sensor communication tool. Identification retrieval and on the spot software download into the reader therefore becomes possible. Using this dual technology approach, almost any type of sensor can be combined with a RFID tag as described in this application. As will be discussed herein, the sensor is adapted to respond to virtually any stimulus and communicate information pertaining to the stimulus wirelessly. The underlying principles of the technology are described in more detail in U.S. patent application Ser. No. 10/761,362, filed Jan. 22, 2004, entitled "Radio Frequency Identification Based (RFID) Sensor Networks," that is incorporated herein by reference in its entirety.

Figure 1:
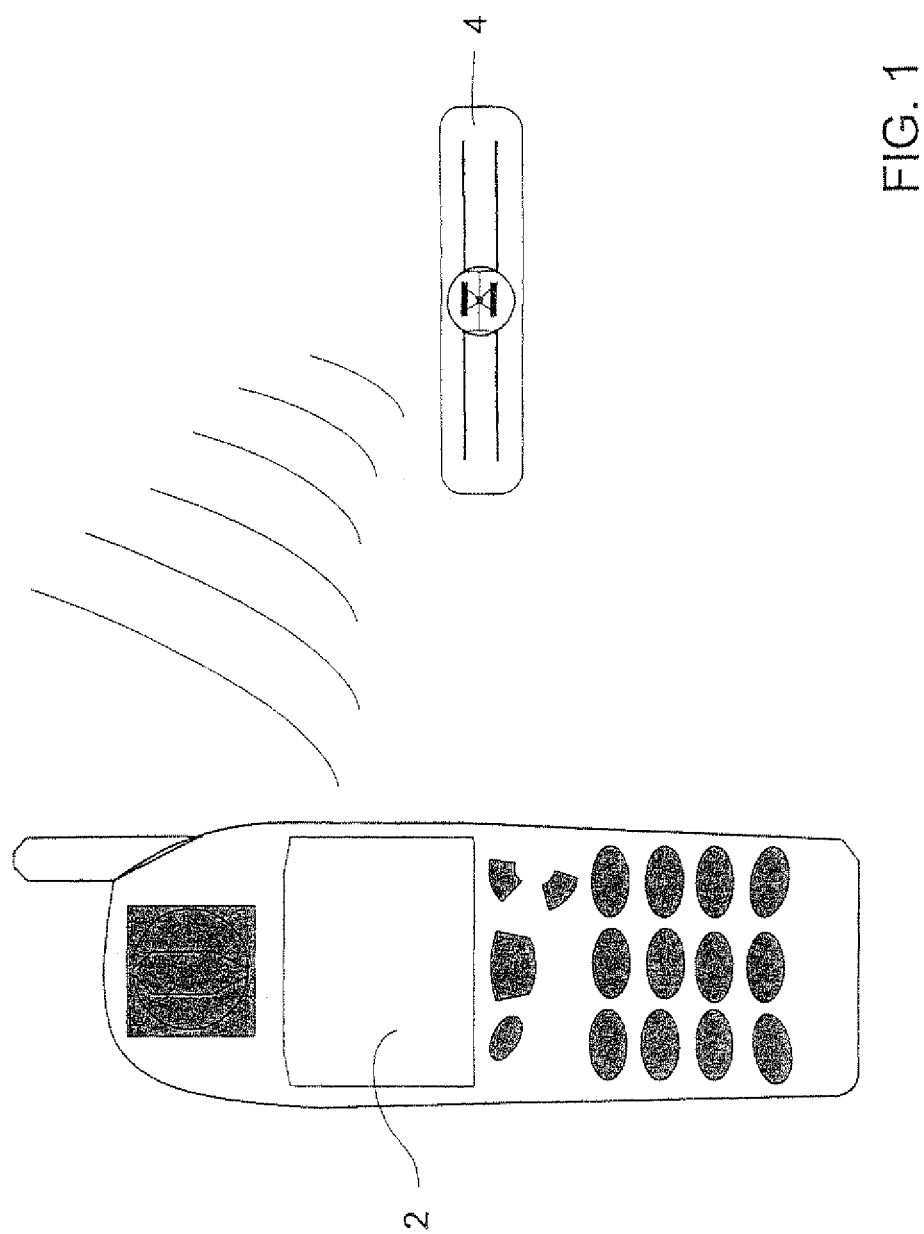
FIG. 1 depicts a block diagram of a modified cell phone serving as a radio frequency identification (RFID) reader with an RFID tag that is embedded in a disposable skin patch according to an embodiment of the present invention.

FIG. 1 is a block diagram of a modified wireless device typically a cellular phone 2 that includes a microprocessor and the necessary logic to serve as a "power up" and read device for a passive RFID tag that is mounted directly inside a disposable patch 4. As it is made clear in U.S. patent application Ser. No. 10/761,362, filed Jan. 22, 2004, entitled, "Radio Frequency Identification Based (RFID) Sensor Networks," any modified wireless device can be used. For example, in lieu of a modified cell phone an RFID reader can be used and may include the necessary data processing, remote access and wireless link capabilities present in devices such as a cell phone. Furthermore devices such as a modified wireless PDA, a modified wireless computer, a modified cordless phone, a modified beeper or even a modified wireless watch may also be combined with RFID technology and be used as readers. In addition, as indicated above, the principles described in this application may be extended to technologies other than RFID. For example a cell phone that is Bluetooth equipped may be used to communicate with and power a remote modified wireless Bluetooth chip that is combined with the diagnostic sensor technologies described here.

Ideally the RFID electronic chip technology is fully compatible with international RFID readers and tag standards making the technology completely universal and transparent in any country or for any class of RFID chip. At the present time these include Class 0, Class 0+, Class 1 and Gen-2 standards. Emerging RFID standards are referred to as Generation 2 or Gen-2 but other standards may emerge and be adopted in the future. It is one of the objectives of this technology to be compatible with as many standards as possible so that a modified cell phone or PDA can read any given RFID tag or RFID sensor tag anywhere in the world. A multi-protocol RFID reader can be used and be compressed on a single electronic chip or be directly incorporated into the core chipset of a cell phone or wireless device. For example, the multi-protocol reader technology can be included into a 3G electronic chip with the Bluetooth protocol so that any 3G device can read any RFID electronic product code (EPC) tag, RFID sensor tag or Bluetooth sensor chip transparently. The cell phone or personal wireless device has remote access capabilities integrated therein. Thus a cellular telephone user can dial up any remote database or the Internet to access data from the RFID tag. In addition to having these capabilities and having RFID reading capabilities, the device may have other Internet access protocols such as Bluetooth, Wi-Fi, Broadband, WLAN, 3G or other emerging technologies that may allow free or low cost Internet access. Using these technologies will be particularly beneficial to fully exploit the full potential of the present invention.

Patch 4 is typically attached to a subject (e.g., a person) but may also be attached to any location, device or object according to an embodiment of the present invention. In one embodiment, the stimulus may be temperature and the RFID tag and patch combination form a smart wireless temperature sensor. Accordingly, temperature can be directly measured remotely on a modified cell phone that can be used to process RFID data and warn a user of a wireless device about a temperature in a subject remotely. The patch is therefore a "smart" patch and the wireless device becomes a "smart" device in combination with the RFID-sensor. An example of an application is a worker or a firefighter who can self-monitor him or herself for heat stress and/or toxic fumes using a cell phone with RFID read capabilities. If the cell phone is Bluetooth equipped, in addition to doing sensor analyses, it may also send signals to both the firefighter directly into his or her ear but also remotely to a monitoring station. In addition as explained in U.S. Pat. No. 6,031,454, that is incorporated herein in its entirety real time precise geolocation of the firefighter is possible.

Another example of an application for this technology is remote monitoring of a fever in a child or patient using a dedicated cell phone or similar wireless device that can be used to call another cell phone and warn a parent or a nurse of a temperature build-up in a given patient. For example a parent can place smart skin patch 4 on the forehead of a sick child and leave a device 2 to monitor the child remotely while the child and the parent are at sleep. If the child develops a fever during the night that reaches a pre-set threshold device 4 will automatically warn the parent and the warning may be done in any remote location. In one embodiment the smart patch is used in hospitals and can remotely monitor a number of patients simultaneously. With the recent FDA mandate that drugs be labeled with RFID tags, both patients, drugs and in fact anything can be monitored in real time in "smart" hospitals. The readers in a hospital allow geolocation and therefore real time monitoring of the entire events in the hospital. Readers may also be directly connected to a network, thereby offering great flexibility in the infrastructures that are used. In one embodiment the temperature skin patch is a smart Band-Aid.

In another embodiment of the present invention the RFID tag and skin patch combination includes a plurality of sensors that can be combined for different diagnostic applications that can be measured directly on the surface of the skin, transdermally, in skin sweat, in blood drawn directly onto a disposable skin patch. In another embodiment the skin patch may also be used to measure external parameters such as physical, chemical or electrical parameters or a combination thereof on a patient. For example the RFID skin patch may be used to monitor the heart or be used to monitor external factors affecting the skin such as radiation.

Figure 2:
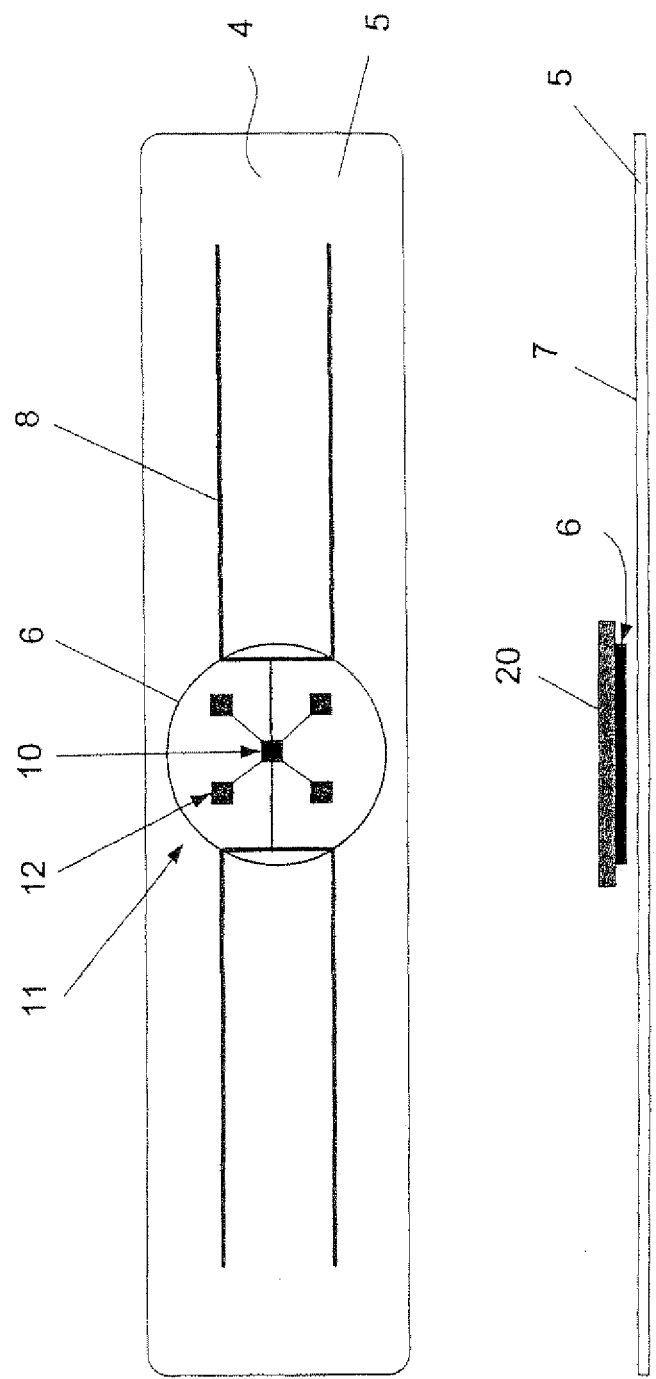
FIG. 2 depicts a block diagram of a disposable fully integrated skin patch having an RFID tag and sensor module that includes an electronic chip, sensors and an antenna according to an embodiment of the present invention.

FIG. 2 is a block diagram of a smart skin patch. As illustrated, patch 4 has an RFID tag and sensor module 11. RFID tag and sensor unit 11 combines an RFID tag with at least one sensor. Specifically, RFID tag and sensor module 11 includes an RFID electronic chip 10, a sensor 12, and at least one antenna 8. Typically the patch 4 is composed of a thin flexible support 5 that has an adhesive surface 7. Onto support 5 is mounted an antenna 8 typically composed of either a thin flexible metal film such as aluminum or material that is printed using doped inks or other flexible and highly conductive materials such as conductive polymers. The antenna may be printed on the external surface of the skin patch to avoid any possible skin contact or contamination.

Antenna 8 powers RFID electronic chip 10. In one embodiment RFID electronic chip 10 is passive. Alternatively, as recognized by one of ordinary skill, RFID electronic chip 10 may be active. In either case, RFID electronic chip 10 is typically located on a disk 6 that includes one or more sensors 12. RFID tag and sensor module 11 form an integrated unit on substrate disk 6. Disk 6 may be either a flexible substrate such as a plastic or a rigid disk that includes different types of semiconductor sensors. For example disk 6 may include a combination of an RFID tag and another low power sensor on a silicon substrate, whereby the RFID tag serves as power and wireless unit and the sensor serves as the sensing element. The term RFID tag refers to the combination of antenna 8 and RFID electronic chip 10. Power may be stored into the passive electronic chip by multiple cycles of external radio frequency (RF) energy. Using the combination of an RFID passive tag and energy storage capabilities complex sensors may be combined with RFID tags directly on a disposable skin patch. These sensors do not need any internal power, are disposable and can be geolocated. Typically the manufacturing cost will be less than $1, resulting in great savings, convenience and improved safety.

Typically disk 6 and sensing elements 12 are protected by at least one protective layer 20. Accordingly, when patch 4 is positioned on the skin, layer 20 makes direct contact with the surface of the skin. Layer 20 may be semi-permeable and may include specific chemistries that, in combination with the chemistries on each given sensor 12, aid in the detection of specific chemical or biological elements. For example protective layer 20 may filter certain proteins or cells and, at the same time, prime the chemistries for specific reactions on the sensor or sensors according to one embodiment.

In addition disk 6 may also include more complex sensors that optically detect changes in blood chemistries and may include one or more diodes combined with sensors (not shown). For example small Schottky or back bias diodes may be used. Additionally using advances in polymers and other thin film technologies complex low power sensor-reader combinations may be printed or produced at very low cost. More complex sensors that are built directly on the electronic chip or an add-on electronic chip may also be used in the smart skin patch.

The smart patch technology described here can therefore perform any number of different tests on a subject and be processed remotely by a wireless device such as a cell phone. The wireless device provides not only the power but also provides the means to analyze and process the sensor data on the spot. Therefore the processing requirements of the RFID tag and the sensing element are reduced, thereby reducing cost and power requirements and making the technology disposable. The wireless device can also provide step-by-step instructions to a user for each given type of sensor. Since the RFID tag provides a unique ID to the wireless device this ID identifies uniquely the type of sensor used. New classes of RFID sensors may also become part of the emerging international RFID standards and have unique sensor identifiers. The data tables 68 are also capable of storing the identification number of each sensor. Additionally, the data tables 68 that analyze any given sensor may be stored on the chip, inside the cell phone or remotely. Therefore any cell phone can analyze on the spot any type of RFID EPC tag or RFID sensor tag, regardless of the manufacturer and as explained more fully in this invention.

Figure 3B:
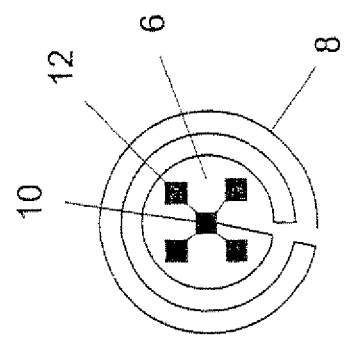
FIG. 3B is an alternative embodiment of the RFID tag and sensor module shown in FIG. 2.
Figure 3A:
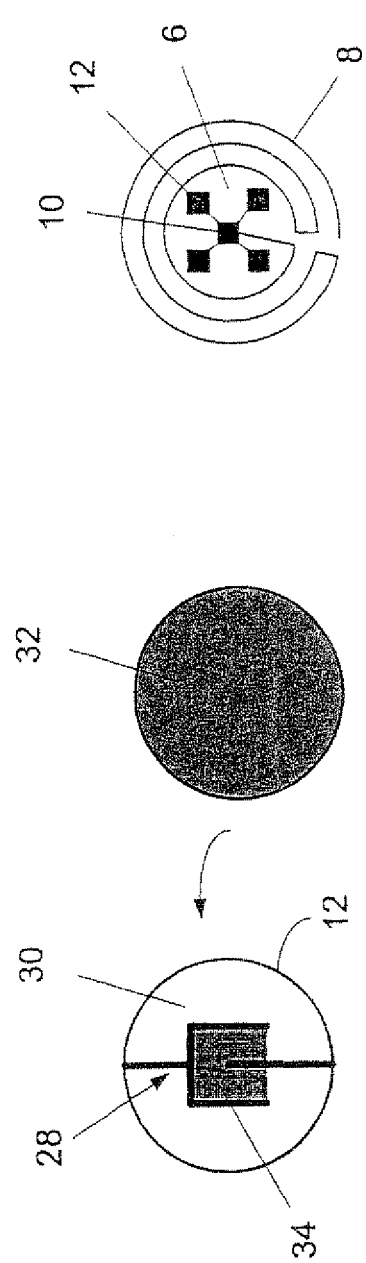
FIG. 3A is a detailed illustration of the sensor shown in FIG. 2 including a chemical/physical barrier.

FIGS. 3A and 3B illustrate different types of elements that can be included on skin patch 4. FIG. 3A describes one type of sensor 12. In this case a sensor surface 34 is surrounded by conductive electrodes 28. Typically both are directly printed or deposited on a non-conductive surface 30. Methods for printing sensors are well known to those skilled in the art. As indicated above sensor surface 34 can be protected by another chemical layer or physical-chemical barrier 32 that can help filter or eliminate certain elements or refine chemical reactions that will occur on sensor area 34. Multiple layers of barrier or reactive surface 32 (not shown) can be used and can be layered one on top of the other serving as a method to separate different types of molecules and serving as reactive surfaces to absorb, eliminate or modify target molecules or reagents. Furthermore since disk 6 may be rigid, sensors and separating layers may include metals, surfaces with nanopores or any element comprising a simple or complex multilayer sensor.

In addition different types of sensors can be used including sensors serving as reference or calibration sensors. Since power is provided by the passive RFID tag, any type of sensor or sensor combination can be used on the skin patch to respond to stimuli such as any type of external chemical, electrical or physical changes that can occur on the surface of the skin. It is recognized that responding to stimuli includes any measuring, detecting, and/or reacting by the sensors.

Nevertheless, the orientation of disk 6 comprising the sensors may either face towards the skin or face away from it, depending on the given sensor application. In one embodiment the sensor may include a microelectronic circuit that can include for example at least one a diode or other optical means to do complex sensor analyses. Such sensors may be necessary for some applications of the technology where more simple sensing chemistries are not suitable. It will be appreciated that some of these sensors may be built directly into the RFID electronic chip itself. This includes for example a programmable temperature sensor but may also include sensors that measure motion or small electric pulses on the skin. In one embodiment the skin patch is a cardiac sensor. In another embodiment the skin patch measures an external hazard to the skin or subject, such as radiation. In yet another embodiment the RFID skin patch includes a plurality of diagnostic sensors.

FIG. 3B shows disk 6 as an entire integrated unit that comprises a coiled antenna 8, RFID electronic chip 10, and multiple sensor elements 12. The antenna can be mounted on one side of disk 6, while the sensors can be mounted on the other side. Using this approach and according to one embodiment, the integrated unit can be directly mounted onto a support 5 in a one step process.

Figure 3C:
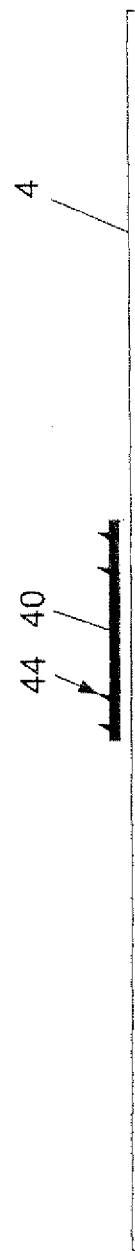
FIG. 3C illustrates a disposable skin patch that is adapted to draw blood from a subject.

FIG. 3C shows another embodiment of the present invention. In this case skin patch 4 also includes a hard surface 40 that includes one or several micro knives 44 meant to help draw a drop of blood into the sensor areas (not shown). Applications of this technology may include any diagnostic test where blood needs to be drawn. A disposable skin patch with RFID sensors that includes the micro knives would simply need to be pressed slightly on the skin to draw sufficient blood for an analysis causing minimal pain to the patient. The skin patch may even include a chemical to neutralize pain in the immediate area where blood is drawn. Once the patch is applied to the skin a read of the sensor is taken from wireless device 2. In one embodiment this wireless test using an RFID sensor is applied to blood glucose monitoring using a disposable RFID-skin patch and wireless device combination. If blood is drawn the sensor elements may include a filtering and separation mechanism (such as a surface with micro or nanopores). Furthermore in another embodiment the RFID sensing element may be separated from the blood drawing element and is reusable. The sensor element may then be more complex and may be included for example directly into a watch.

In addition non-invasive methods to measure glucose levels or other bodily chemistries may also be used and combined with RFID technologies. These include the use of diodes or other optical means that can detect optical-chemical changes that occur.

FIG. 4 shows how a skin patch 4 that includes RFID tag technologies, the proper sensor chemistries and a mechanical device as described in FIG. 3C can be used in case of diabetes self-monitoring and insulin self-regulation using a modified wireless device such as a modified cell phone 2. Data is obtained from a disposable skin patch and processed by the microprocessor of a cell phone. In one embodiment the cell phone can then control via RF a remote insulin pump 50 that can be implanted in a body. In lieu of using a separate glucose monitoring device, periodic glucose tests are done directly on a modified cell phone using disposable RFID-sensor skin patches. This way the patient does not need to use two devices and can check directly abnormal results with his/her doctor in case of need. In some cases the skin patch may be reusable using reversible reactions on the sensor surfaces. In one embodiment reversal occurs by micro heating the sensor area using power provided remotely by the wireless device. The implications of the invention shown in FIG. 4 is that any RFID or Bluetooth sensor can be read by a device like a modified cell phone that can also serve as a control system for other wireless technologies that are dependent on sensor values. Device 2 may also allow direct remote monitoring of a given patient for other functions, remote alerts and access to a physician's Office or medical center. For example the device may monitor cardiac function on the smart skin patch, patient temperature, position, etc.

Figure 5:
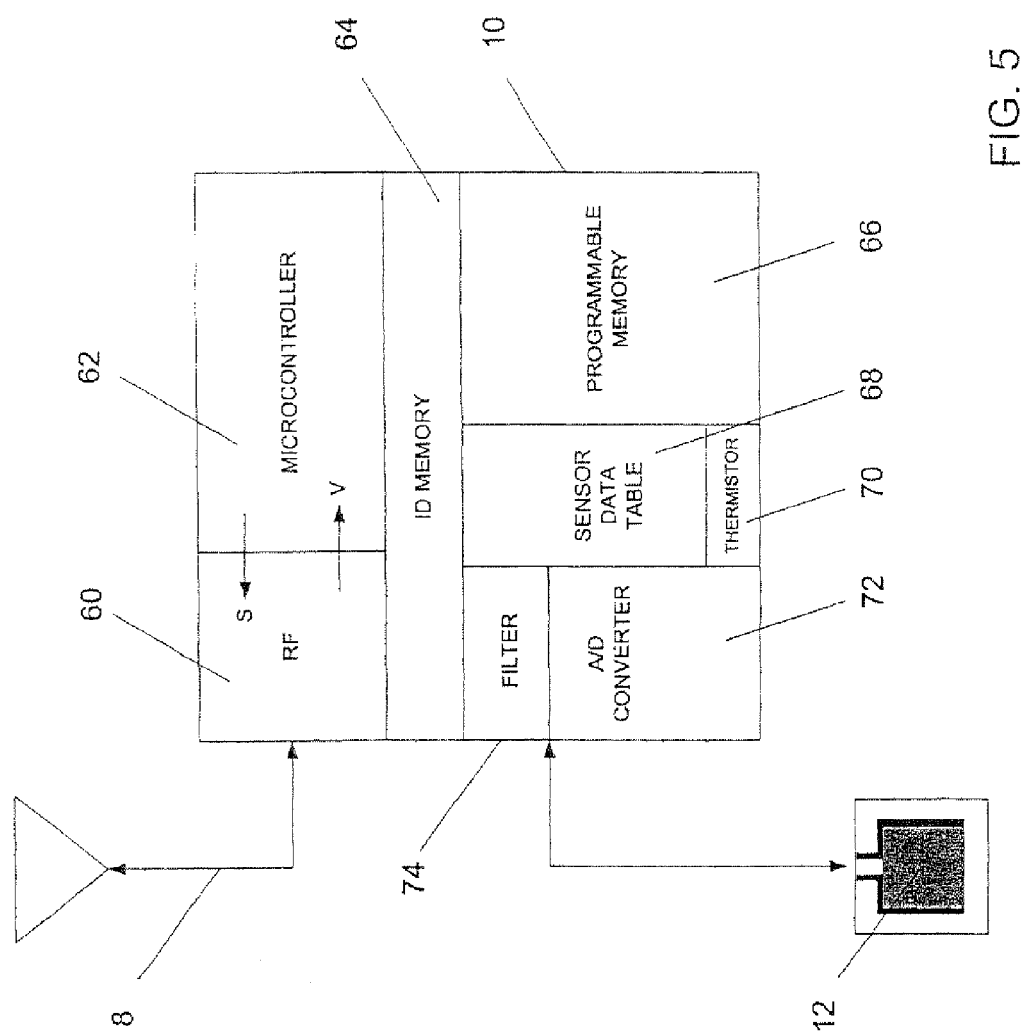
FIG. 5 is a detailed block diagram of the RFID tag and sensor module that includes the electronic chip, the antenna and the sensor of FIG. 2.

FIG. 5 shows the basic elements of the RFID electronic chip 10. RFID electronic chip 10 is coupled to antenna 8 that may include separate send and receive elements (not shown). As discussed above, the combination of RFID electronic chip 10 and antenna 8 is referred to as an RFID tag. Antenna 8 may be printed directly on a polymer or plastic substrate. The principles and operation of the RFID tag having a sensor input is described in detail in U.S. patent application Ser. No. 10/761,362, filed Jan. 22, 2004, entitled "Radio Frequency Identification Based (RFID) Sensor Networks," which is incorporated herein by reference in its entirety. Additional reference is also made to U.S. Pat. No. 6,720,866 B1.

Antenna 8 is connected to a power unit 60 with a voltage stabilization circuit, a controller 62, an identification unit 64 (which may be permanent or programmable), a memory unit 66, a sensor table 68, a thermistor or temperature module/sensor 70, and analog to digital converter 72 and an optional filter 74. Preferably, the temperature sensor 70 of the RFID electronic chip 10 is a very low power, highly accurate programmable unit that enables precise reference and calibration points for any application of RFID tag and sensor module 11. In addition, the electronic chip 10 may include an energy storage unit (not shown) that stores energy for the power unit 60. This is important for sensors that exceed the available power to the passive chip. The device may be a Class 0 electronic chip as described in U.S. Pat. No. 6,002,344, a Class 0+ chip, a Class 1 chip, a Gen-2 electronic chip or any other RFID or Bluetooth electronic chip that serves as a basic platform and is modified to include a built-in precise temperature unit, a voltage stabilization unit, an A/D converter and the ability to incorporate at least one or a plurality of sensors that are then incorporated into the devices described in this invention and form the basis for passive RFID-diagnostic sensors that can be directly read by common low cost wireless devices such as modified cell phones. Using the passive approach approximately 10 µwatts of power is available to the sensors from the RFID chip 10. Furthermore voltage can be precisely regulated in the range of 1-5 volts, providing adequate power to most diagnostic sensors.

The RFID electronic chip 10 is attached to one or multiple external sensors 12 that receive power and are controlled by units 60, 62, 72 and 74. Sensors 12 and part of the electronic circuitry may be composed of low cost doped inks or conductive polymers as described in U.S. patent application Ser. No. 10/382,606, entitled "Method and Apparatus for Wide Area Surveillance of a Terrorist or Personal Threat," which is incorporated herein by reference in its entirety.

Figure 6:
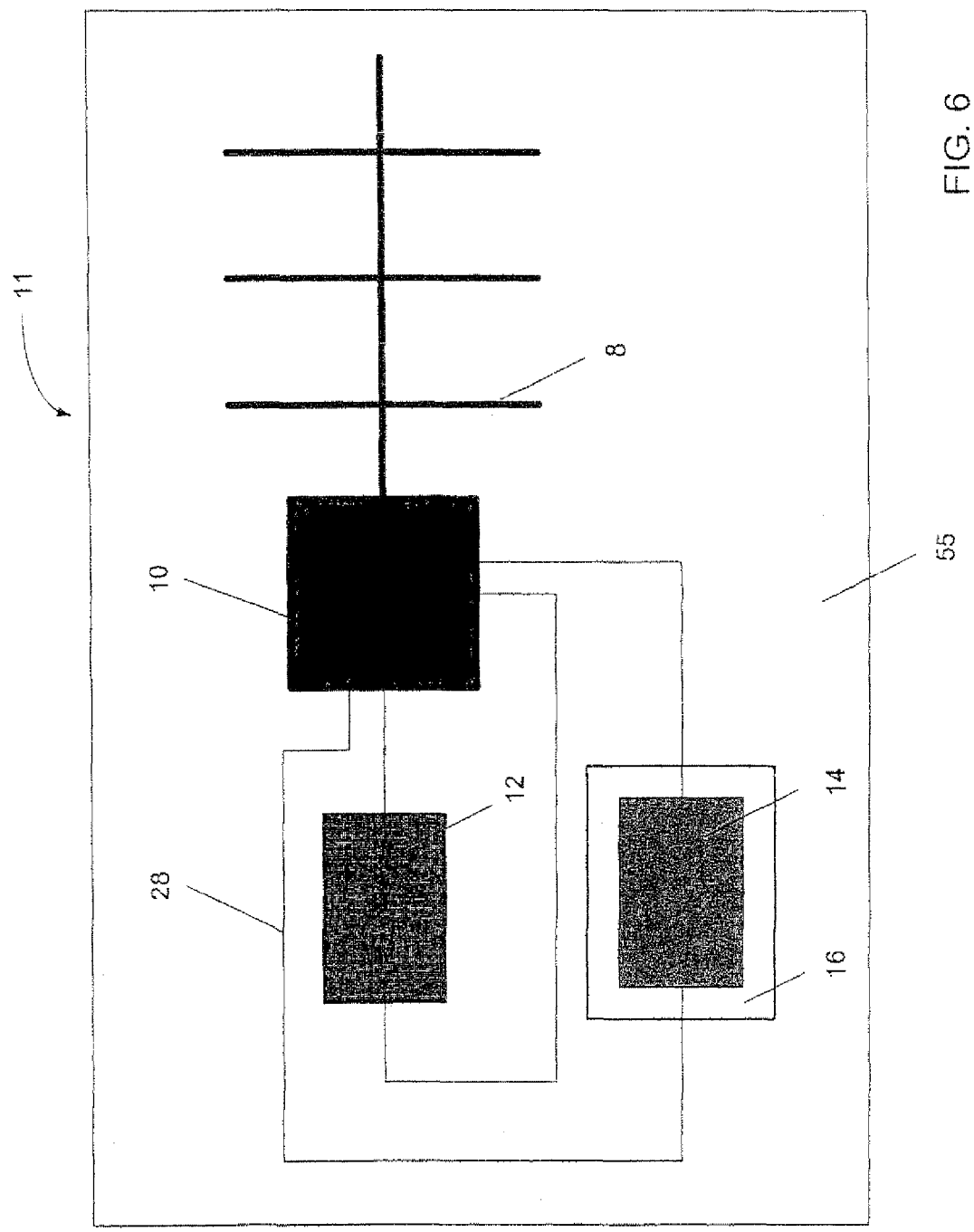
FIG. 6 is yet another block diagram of a RFID tag and sensor module.

FIG. 6 illustrates another embodiment of RFID tag and sensor module 11, which includes RFID electronic chip 10, antenna 8, a substrate 55, conductive leads 28, and a sensor element 12. For a number of applications, particularly diagnostic applications, at least one reference element 14 is used. In some applications the reference element or the sensor may include at least one optional shield 16. In one embodiment the shield 16 is a light shield that covers a radiation sensitive film to be used for a low cost radiation RFID tag and sensor module 11 that may be included in a skin patch for a patient or may be used for Homeland Security or defense applications. In one embodiment both the RFID tag and elements 14 and 16 serve as radiation detectors. Several types of radiation sensitive polymers or other thin film materials may be used and be printed directly on the antenna substrate, creating a very low cost RFID passive radiation sensor. Since different types of radiation sensitive materials may be used, both qualitative and quantitative radiation sensors can be produced at extremely low cost. Additionally radiation sensing diodes may be included directly in chip 10, providing further low cost means to detect a radiation hazard.

In one embodiment sensor 12 is a chemical sensor. Therefore both low cost chemical and radiation detectors can be included on a low cost disposable substrate that includes a wireless RFID tag and power unit.

Figure 7:
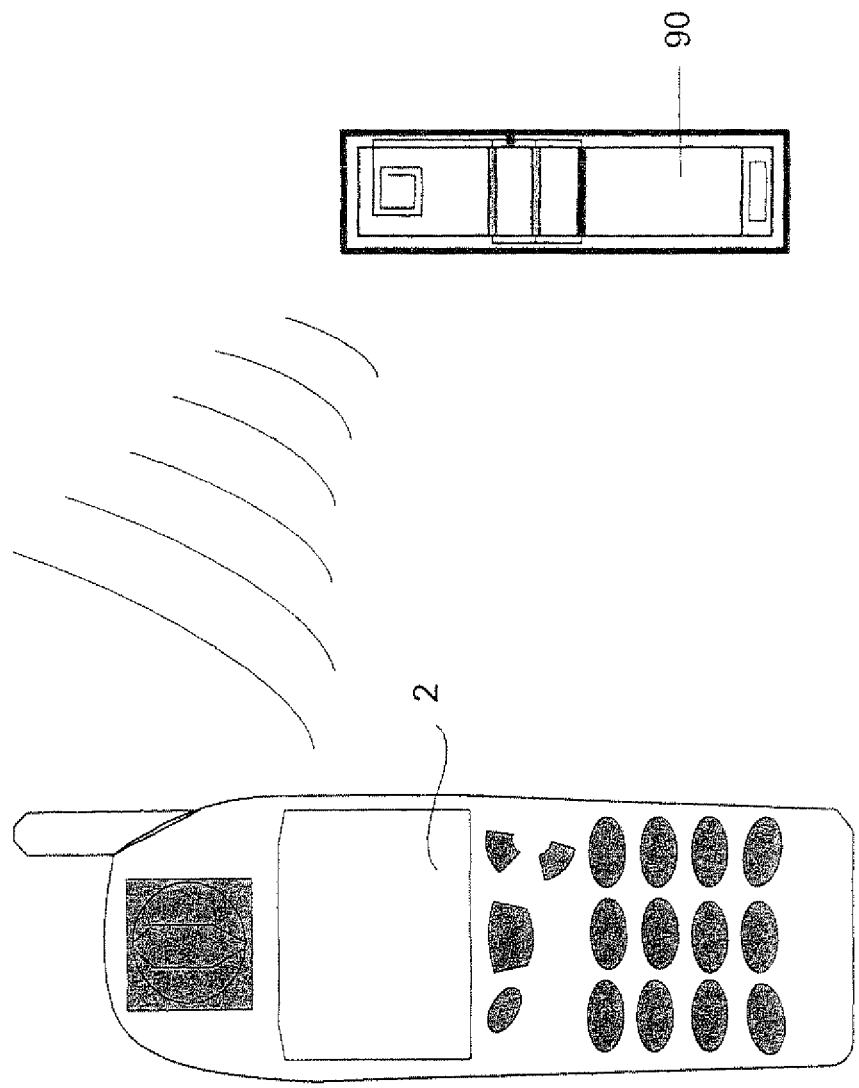
FIG. 7 depicts a system diagram of a modified cell phone that serves as a RFID reader for a disposable diagnostic flow-through RFID immunoassay strip.

FIG. 7 shows the applications of another type of novel RFID-sensor technology combined with disposable flow-through assays to form a disposable wireless passive RFID immunoassay. Such assays can be included in disposable kits 90 where the power is provided remotely by the low cost wireless device 2 and the analyses are also performed on said device or remotely via wireless links.

Figure 8:
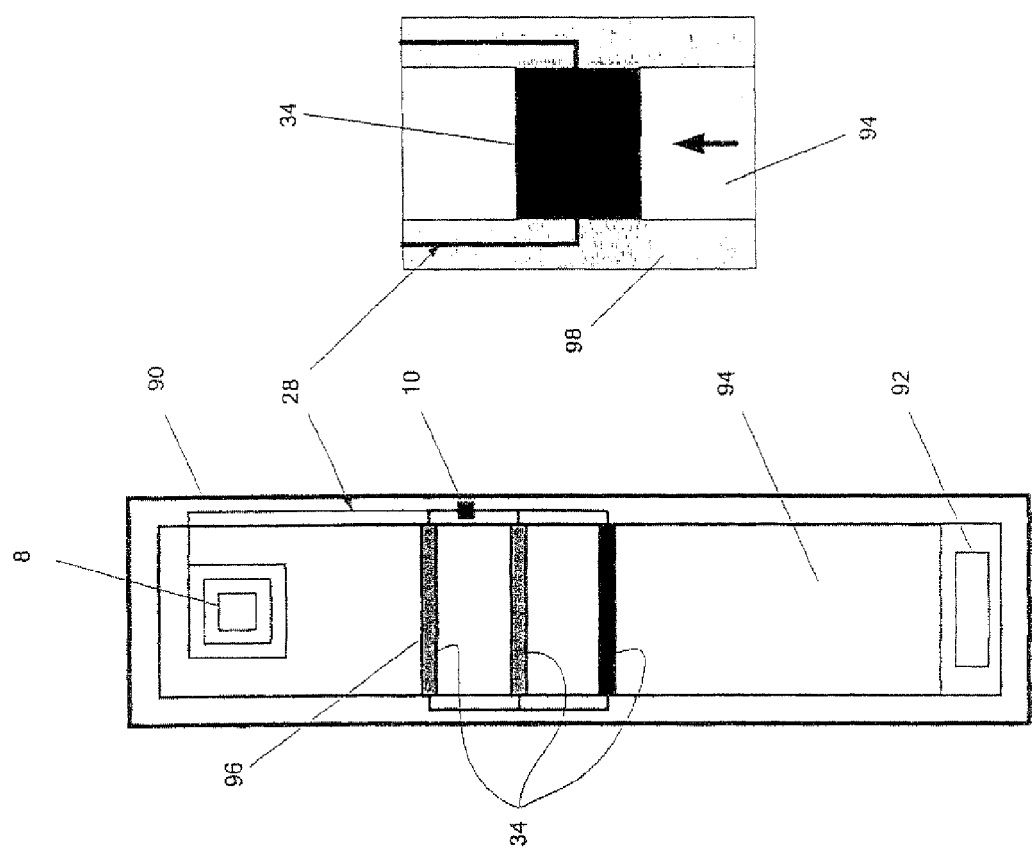
FIG. 8 is a detailed illustration of the immunoassay strip shown in FIG. 7.

FIG. 8 describes the technology of FIG. 7 in more detail. A flow-through immunoassay testing strip 90 includes a sample input port 92 and a substrate 94 that allows migration of the analyte on the assay by capillary forces. The assay includes one or multiple test areas 96 that are typically immobilized antibodies serving as a capture surface for specific antigens that flow through the test surface. Such tests are now commonly used to test for pregnancy, for the presence of specific proteins or toxins and for the detection of specific pathogens such as *Streptococcus*. Recently with the discovery of disease-specific biomarkers more complex tests are starting to become available. However using visual methods, such tests do not provide precise quantitative results and therefore is still generally limited to "yes" or "no" assays indicating simply the presence or absence of a given protein or bio-analyte. While tests have improved greatly to the extent that they have now been placed in the hands of the public the quantification of the presence or absence of given proteins remains a highly desirable goal. Such quantification can be now achieved by adding RFID or Bluetooth technology as shown in the present invention. An RFID electronic chip 10 is added onto disposable device 90 and includes conductive leads 28 that go either to antenna 8 or to sensor areas 34. In order to avoid shorting electrodes 28 may be embedded into plastic leads 98 that can also serve as channels for the analyte flowing across sensor area 34. Printing of leads and channels can be done using ink-jet technology or other similar means and is a low cost technology well known to those skilled in the art. Leads may also be laminated or molded directly into plastic substrates. Other low cost assembly or production methods may also be used.

One of the test areas 96 may be a reference test area that measures the amount of moisture present on the surface or the presence or absence of given proteins or other analytes. In some applications the surface has to dry out before the results are read on the wireless device and this can be done automatically by using the reference strip or strips. In addition a window (not shown) may be used with a visual clue as to when the test is ready for analysis. For example if the test surface has to dry out then a simple color change may be used with a hygroscopic material that changes from red to blue depending on the level of moisture present on the RFID immunoassay strip.

Using this method many different channels and tests can be performed simultaneously on a single disposable test strip. Furthermore this technology can be applied to different types of assays such as lateral-flow, flow-through or solid-phase assays or any assay where an analyte is carried across a surface. The methods to fabricate the basic separation surface are well known to those skilled in the art and may include nitrocellulose or other similar materials.

Figure 9:
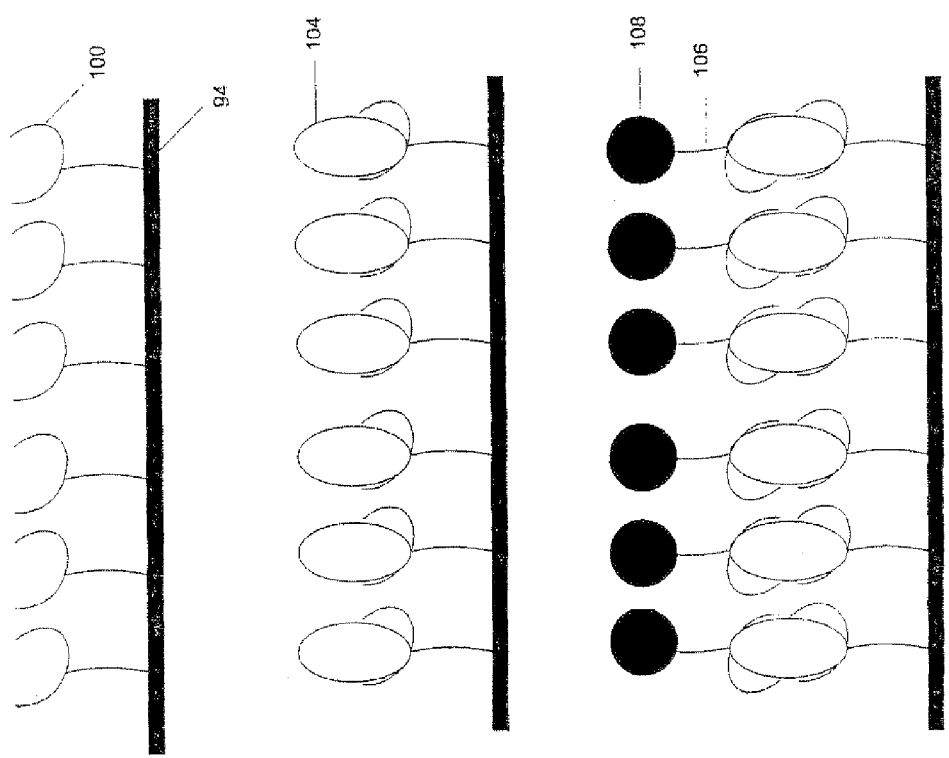
FIG. 9 is a detailed illustration of the sensor area of FIG. 8.

FIG. 9 shows details of sensor area 34. Antibodies 100 are immobilized onto substrate 94 using printing or other standard deposition methods used for the fabrication of lateral-flow assays. As an analyte is carried across the test strip by capillary action, matching antigens 104 become attached to the antibodies. Such antigens could be proteins found in blood or urine, proteins found on surfaces of pathogens or they could be other biological molecules. The technology can be applied to any sensor situation with specific surface-to-surface interactions. In one embodiment this applies to proteins. In another embodiment to DNA or RNA. Hence disposable wireless RFID-sensor DNA assays that are read directly on a cell phone become possible with the technology described in the application.

In order to allow conductivity between the two electrodes present in the sensor area, in some applications another layer of antibodies 106 can be added which are specific to antigen 104. This technique is generally referred to as a "sandwich assay" and different methods exist to conduct such assays. In this case instead of having dyes attached to the antibodies, conductive molecules 108 are attached forming a conductive layer within sensor area 34. Conductive molecules can be conductive nanoparticles, conductive proteins, metal particles that are attached to the protein or latex or other beads that are conductive. As indicated above if DNA or RNA is used then the conductive molecules can be attached directly then the matching DNA or RNA strands. The release of the conductive molecules 108 may be timed such that the assay is a simple, one step process.

In some applications the strip may need washing and drying before the measurement are done. The state of the sensor can be assessed electronically by using one or more reference test areas where the sensor consists simply of a material that absorbs water and therefore allows for the saturation level and status of the entire test surface to be measured. Such measurements can be done remotely by the cell phone using sensor data tables that are either stored on the RFID chip, on the memory of the cell phone or by downloading the correct sensor data tables from a remote location on the Internet or a remote location available through the wireless networks. This method allow on the spot complex analyses to be performed.

Since the electrical conductivity of the surface area can be measured precisely quantitative results become possible on disposable wireless RFID electro-immunoassays. Furthermore the test area can become very small allowing for more tests to be done in a given area and therefore resulting in cost savings. In one embodiment the technology applies to high density DNA or RNA chips that are disposable.

In addition to the conductive methods described above, other methods may be used that rely on RFID or Bluetooth as the basic low cost communication and power platform for a disposable RFID immunoassay. For example optical means may be used to assess the presence and level of a given protein. This is possible because the precise position of deposition of given antibodies is known and can match an optical reader. A dual system may be used where the disposable substrate with the protein or DNA test is inserted into a reader (not shown) that comprises an RFID power and communication module that can be read directly with a device like a cell phone, PDA or computer in a doctors office.

Because it is low cost and is quantitative, the technology described in FIGS. 7-9 have broad market applications. In one embodiment it applies to Homeland Security, where instant checks can be performed by protective forces for example to confirm on-the-spot the presence or absence of a given pathogen. In one embodiment the technology is applied to food safety for the public. For instance, using this technology, trace elements can be detected in foods for people with certain allergies such as peanut allergies. In one embodiment the technology applies to medical self-tests for a given medical condition (e.g. a heart attack). In one embodiment the technology applies to screening for a given medical condition such as a pre-cancer condition.

The technology may also be miniaturized and be applied to micro or even to nanosensors with very small sensor areas with the power provided and relayed by a modified RFID or Bluetooth electronic chip to a remote wireless processing device such as a cell phone.

Figure 10:
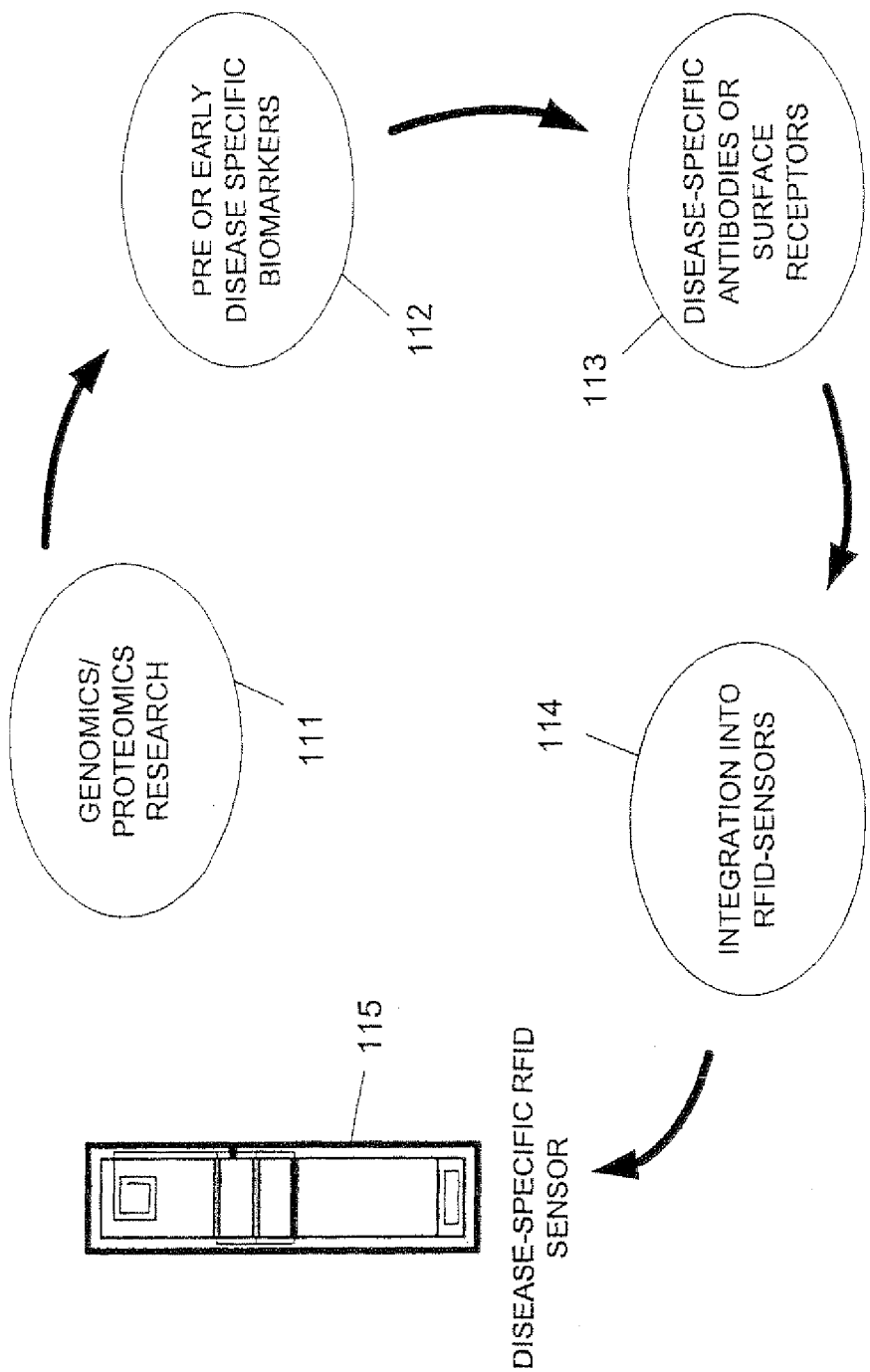
FIG. 10 depicts a method of producing a disease-specific disposable RFID wireless sensor.

FIG. 10 shows the steps involved in the fabrication of disease-specific RFID wireless detection strips. Typically results from Genomics or Proteomics research 111 yield pre-disease or early disease specific biomarkers 112 associated with a given condition. Once these specific markers are identified, disease specific antibodies or surface receptors 113 can be isolated. These are then integrated into disease-specific RFID sensors 114 resulting in a final disease-specific self-contained testing kit 115.

Using the approach described in FIGS. 7-10 any specific disposable wireless RFID test strip can be produced. Since each RFID tag 10 contains its own electronic identification number 64, wireless device 2 can immediately recognize the type of sensor involved and perform the correct analysis. This is because a given modified cell phone can download the necessary software, data tables, etc. from a remote location via a wireless link and can instantly become a "smart" device for any given type of RFID sensor. Furthermore since many different types of tests can be performed at once on the same disposable wireless platform, cross validation and calibration is possible. Because of the remote data access and remote processing capabilities of the wireless reader, the technology described here allows for ubiquitous sensing and analyses for any type of RFID sensor using a single common wireless platform such as a modified cell phone. The RFID-sensors do not need to use a battery and are therefore very low cost. Furthermore for some applications such as remote temperature monitoring the sensor is fully reusable.

Figure 11:
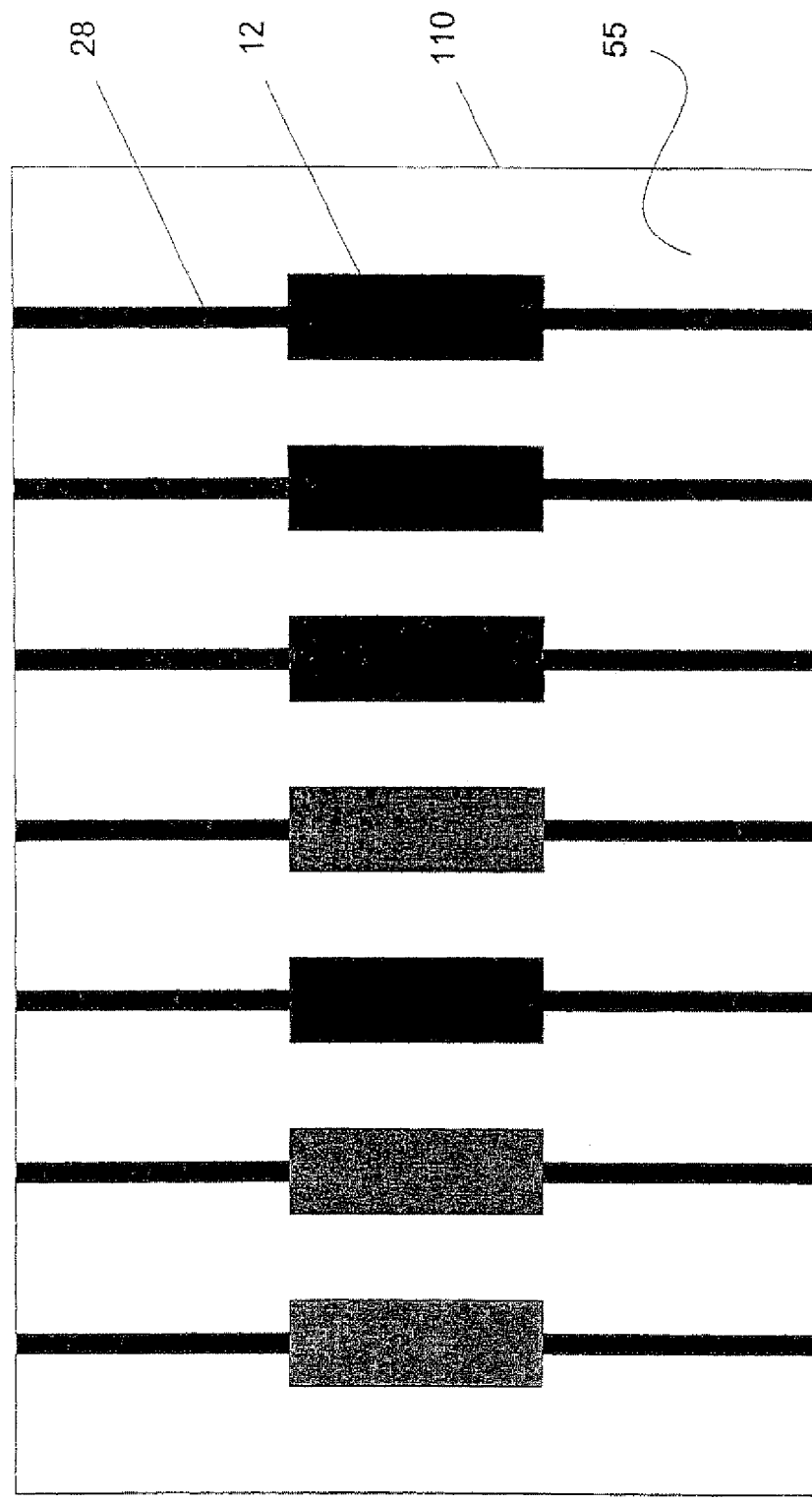
FIG. 11 depicts a block diagram of an array of thin-film chemical sensors printed directly on an RFID substrate according to an embodiment of the present invention.

FIG. 11 shows the application of the technology for the measurement of a number of different gases simultaneously using a single disposable RFID-sensor chip. As part of the antenna substrate 55, an area 110 is composed of a plurality of different sensors 12 with conductive leads 28. Typically each sensor 12 is a different polymer or chemical that can react differently with chemicals present in the air. Because the sensors 12, the area 110 and the RFID electronic chip are on the same substrate, fabrication costs are very low and the entire unit comprising the area 110 including sensors 12 can be assembled in a single step.

Area 110 is typically exposed to the air to allow chemical reactions to take place. In one embodiment the sensor is enclosed in a sealed pouch (not shown) that can be opened at a given time by a user of the sensor to test a given environment.

This "nose" technology and applications thereof is described in more detail in pending patent application serial U.S. patent application Ser. No. 10/382,606, entitled "Method and Apparatus for Wide Area Surveillance of a Terrorist or Personal Threat," which is incorporated herein by reference in its entirety.

Figure 12:
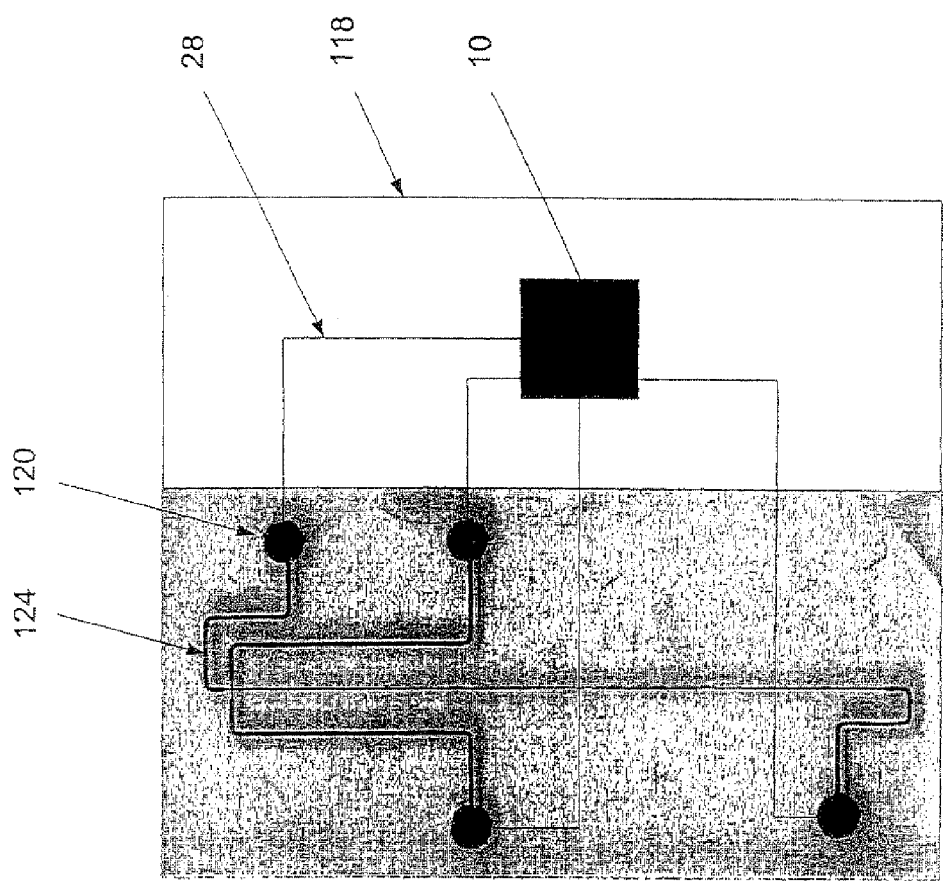
FIG. 12 depicts the integration of RFID technology with Lab-on-a-Chip (LOC) technology according to an embodiment of the present invention.

FIG. 12 shows another embodiment of the present invention relating to Point-of-Care or diagnostic technologies. Specifically it combines lab-on-the-chip (or LOC) technologies with RFID-sensor technology as shown in 118. Lab-on-the chip technology is well described in the scientific literature and consists of multiple microfluidic channels 124 with either test, input or chemical wells 120. Reactions in wells 120 can be measured using RFID technology since conductive leads 28 from RFID electronic chip 10 can be linked directly to each of the test wells 120. An antenna can be printed or mounted in another layer of the electronic chip or directly on the back of the device. Furthermore the leads 28, the antenna and the electronic chip 10 can be embedded into the LOC chip, thereby preventing shorting of the electrodes or electronics. Since LOC allows complex sample separation and analyses, this technology allows LOC tests to be done independently of a complex or expensive reader. Rather a simple wireless device such as a cell phone or a PDA can be used. In one embodiment the cell phone also controls the separation and control of the microfluidics channels 124 for more complex LOC analyses. In one embodiment a LED and other electronic measuring or sensing devices are included in the LOC-RFID chip. Therefore this technology is disposable and allows complex tests that require separation and mixing to be placed directly into the hands of the public.

Figure 13:
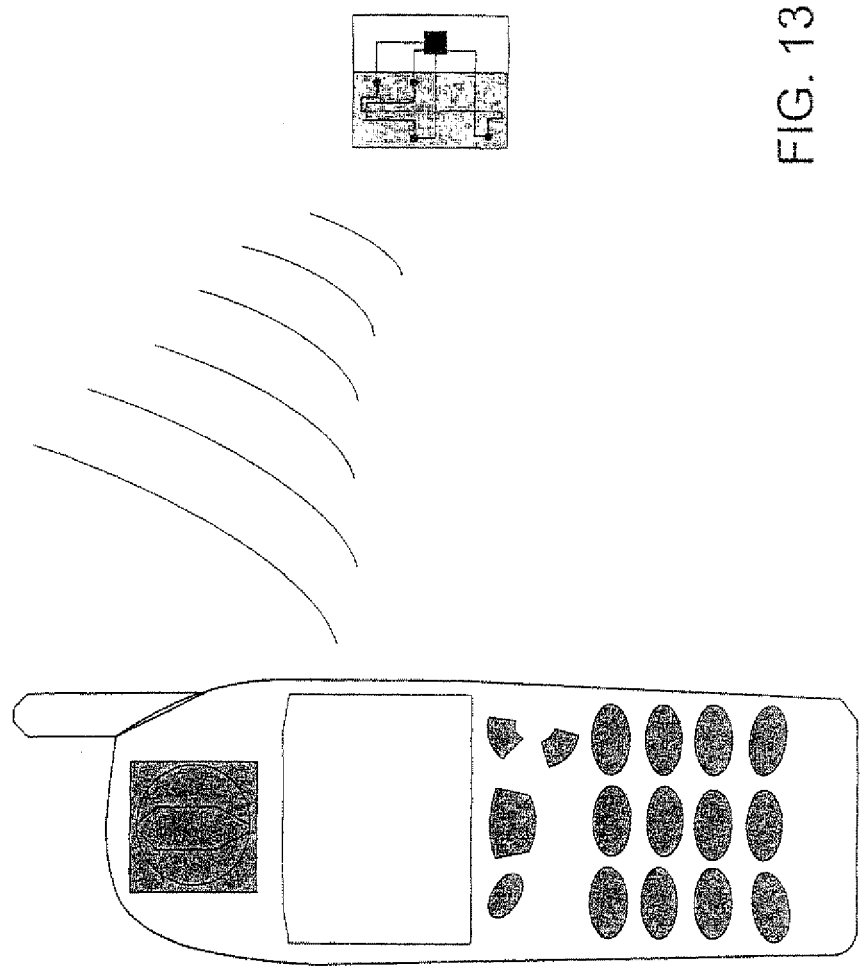
FIG. 13 depicts a modified LOC sensor combined with RFID technology that is read directly with a wireless device such as a cell phone.

FIG. 13 shows how a LOC-RFID sensor unit 118 can be read directly from a wireless device such as a cell phone, thereby bypassing the need for a LOC reader. In the ease of LOC type analyses the data may be complex and exceed the processing capabilities of the low cost wireless reader. In this case the analyses can be performed remotely for example on a remote computer that can be accessed directly via a wireless link. For example a centralized location may be provided with a direct dial in access that is available to user of the cell phone. Other communications systems may also be used. For example, as indicated above, a Bluetooth equipped cell phone, PDA or other device that is also RFID compatible may have a built-in means to directly access the Internet.

Figure 14:
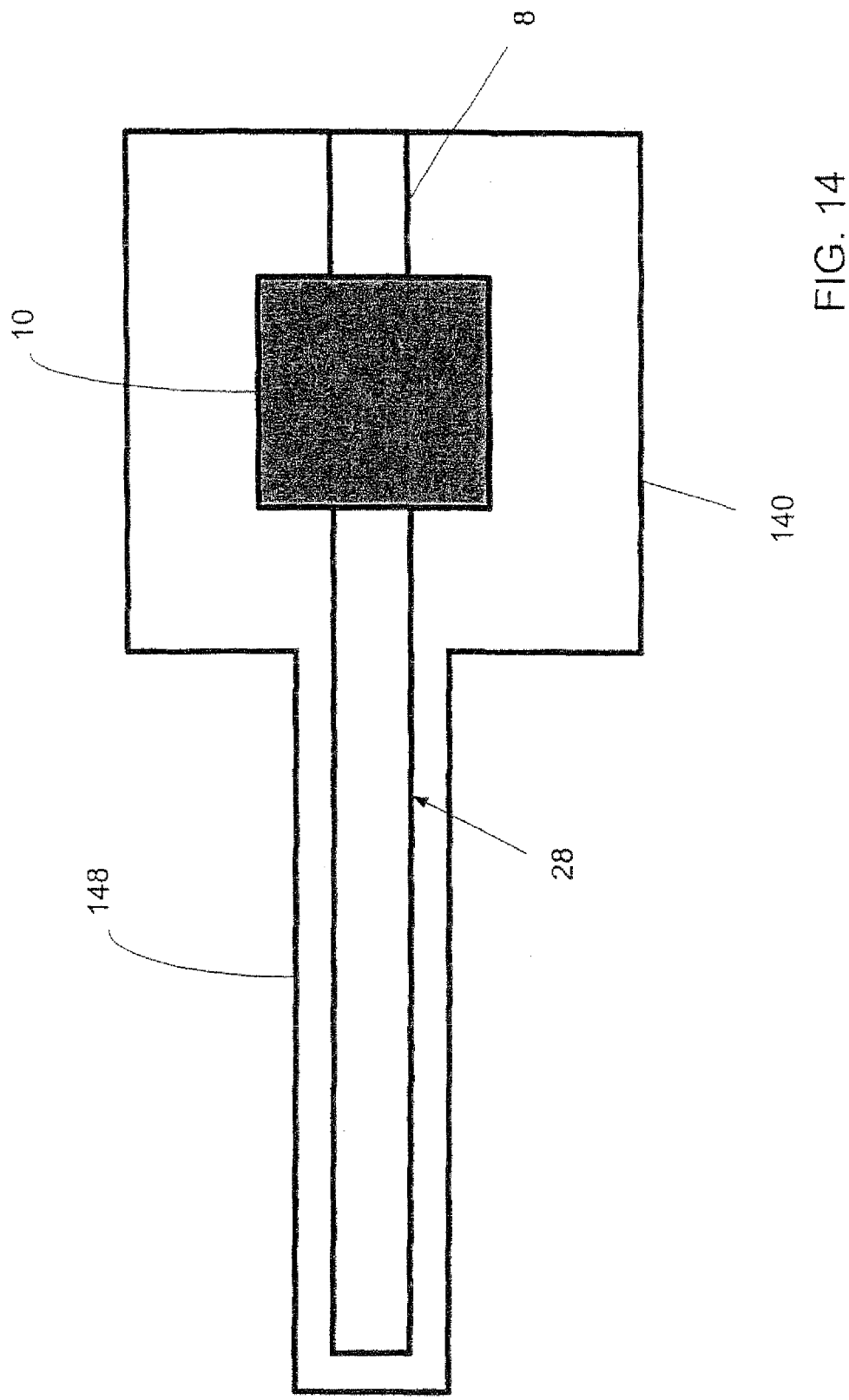
FIG. 14 depicts the integration of passive RFID technology with MEMS sensors according to an embodiment of the present invention.

FIG. 14 shows the integration of Micro Electro Mechanical System (MEMS) sensors 140 with RFID technology. In one embodiment, an RFID electronic chip 10 with conductive leads 28 is combined directly with a MEMS sensor providing the power for the sensor. In one application MEMS sensor 140 includes a resonating surface 148. Antenna leads 8 are only partially shown and typically do not form a part of the sensor area. In this particular case, the leads 28 are exposed to the air and therefore the applications of the technology are more suitable for the detection of gases. However, a number of different MEMS sensor configurations are possible and only one is shown here. Because some MEMS sensors may require more power than what is typically available on an RFID passive chip, the electronic chip may be modified to step up the voltage and/or to store the necessary current required to read MEMS-type sensors. Alternatively, the sensor may include a battery.

Figure 15:
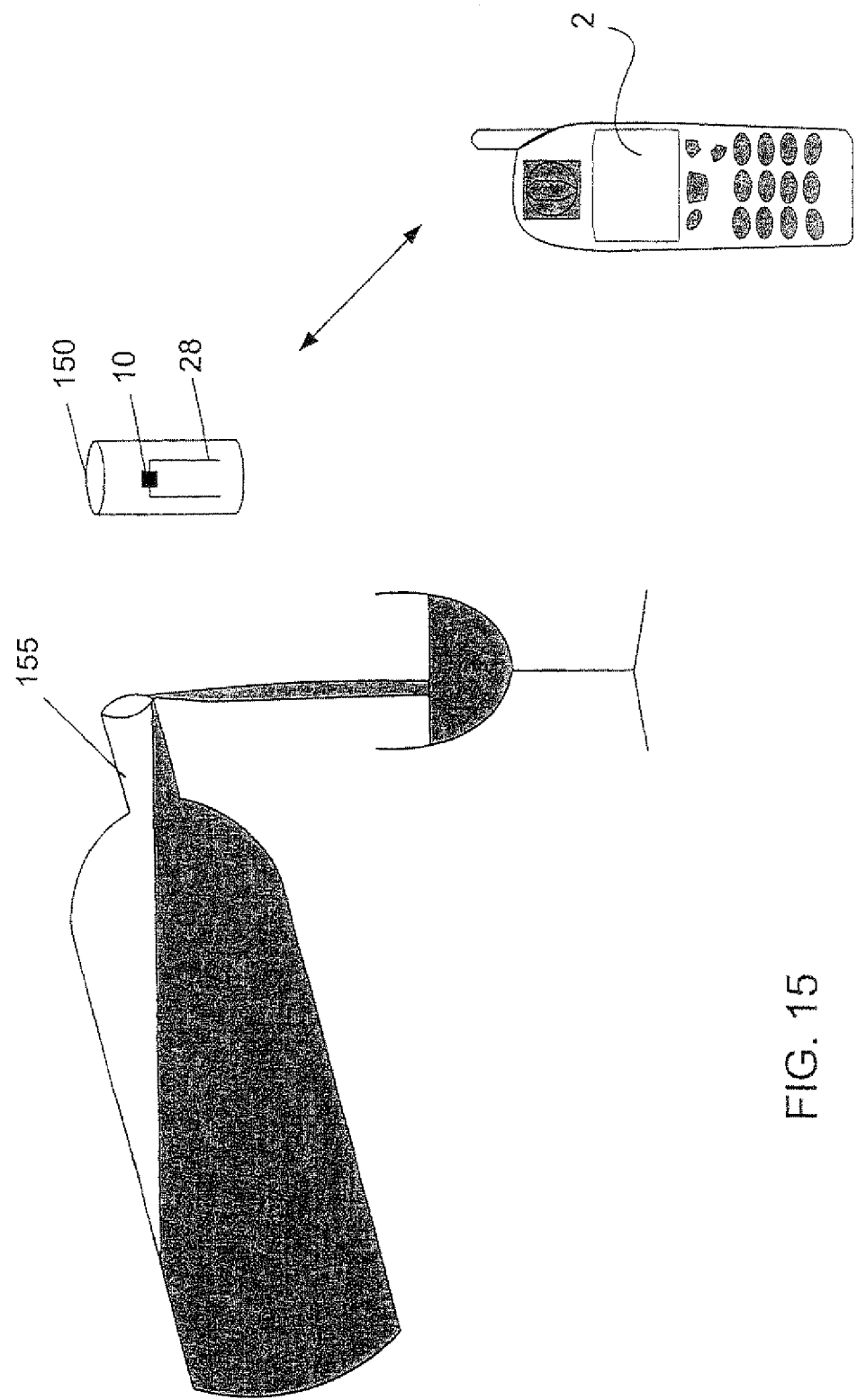
FIG. 15 depicts a wine bottle that includes a cork with a RFID tag and sensor module therein.

FIG. 15 shows the integration of the RFID-sensor passive diagnostic technology applied to foods. In this case the sensor unit 10 is included into a wine cork 150 for "smart wine" applications. In one embodiment, an RFID electronic chip with conductive leads 28 is mounted directly within the cork 150 while the antenna (not shown) is typically outside the bottle and may form a part of the wrapping at the top of the wine bottle. The entire unit is inserted into wine bottle 155. In another embodiment the entire unit with the antenna forms a part of the cork. If the chemistry of the wine changes, the cork will deteriorate because of changes in the acidity of the wine and this can be measured electronically externally with a wireless device such as a modified cell phone 2. Therefore prior to purchase by using a modified cell phone 2 the consumer can immediately spot a bad wine bottle from a good one. Such applications are particularly relevant for expensive wines that must age for quite a while and are subject to many changes in temperature, etc. In another embodiment, the RFID tag technology described herein can include a temperature module and a memory, the entire temperature storage profile of the wine can be recorded on the RFID passive tag and can be retrieved by the consumer on a cell phone prior to purchase. If, for example, the wine was not stored properly this will be known by the consumer. The temperature profile for the wines can be stored on the electronic chip by periodic "power up" cycles or can be stored remotely and retrieved directly from a remote database using the wireless device via a wireless link. Other power and storage means may also be used. Such applications are particularly relevant for "high end" wines.

Figure 16:
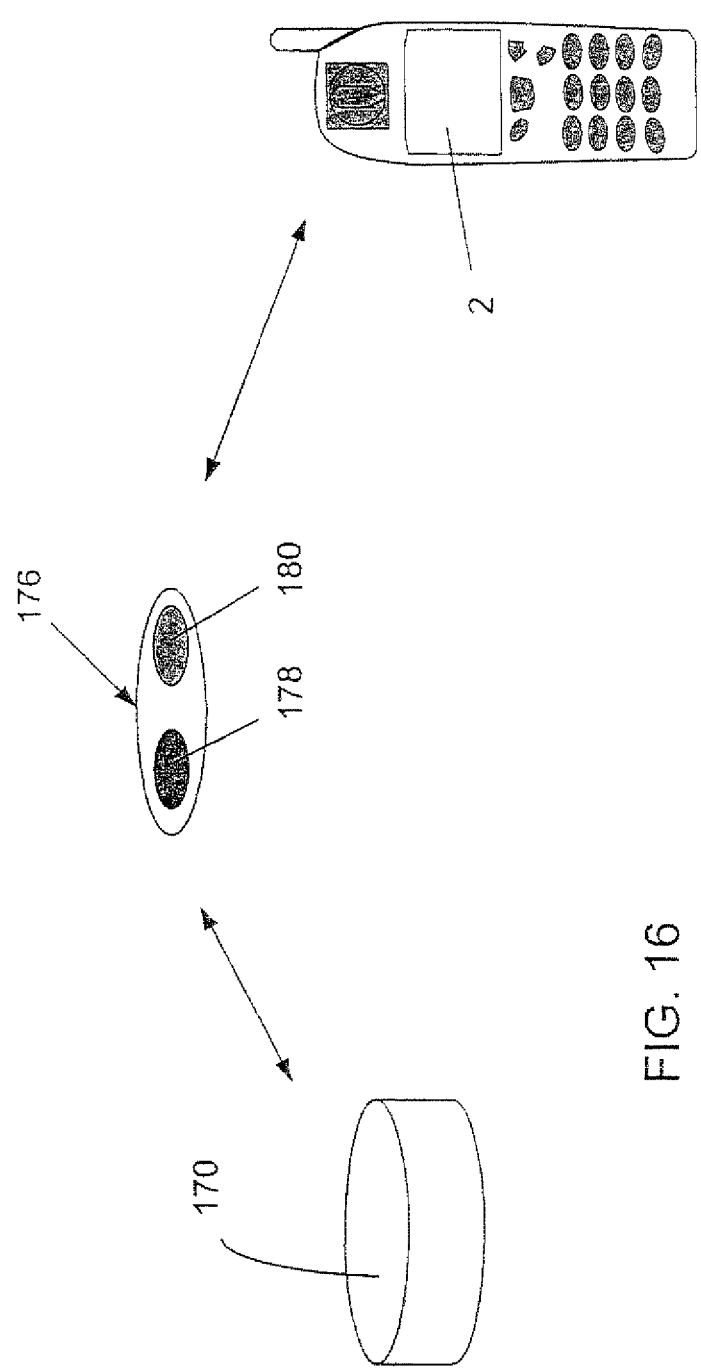
FIG. 16 depicts a smart cheese sensor according to an embodiment of the present invention.

FIG. 16 shows yet another embodiment of the present invention as applied to other food items and in this case "smart" cheeses. Cheeses, like wines, can turn bad without the knowledge of the consumer and prior to opening the package. In this case a cheese 170 includes an electronic RFID label that also includes a sensor pad 176 with at least two sensors 178 and 180. In FIG. 16 neither the antenna nor the RFID electronic chip are shown for the sake of simplicity. One sensor may be composed of a hygroscopic material to determine the moisture level of the cheese 170. The other may be a polymer that is sensitive or reactive to certain smells associated with the aging or degradation of the cheese 170 as a result of bacterial action. If the cheese 170 turns bad it is typically because the moisture level is incorrect or because it has become degraded by bacterial action. By using several sensors a precise assessment of the quality of the cheese can be assured remotely by the consumer prior to purchase using a cell phone 2 with RFID reader capability. The type of sensor ID is matched with data tables and processing instructions that can be downloaded directly into the cell phone. See U.S. patent application Ser. No. 10/761,362, filed Jan. 22, 2004, entitled "Radio Frequency Identification Based (RFID) Sensor Networks," which is incorporated herein by reference in its entirety.

Figure 17:
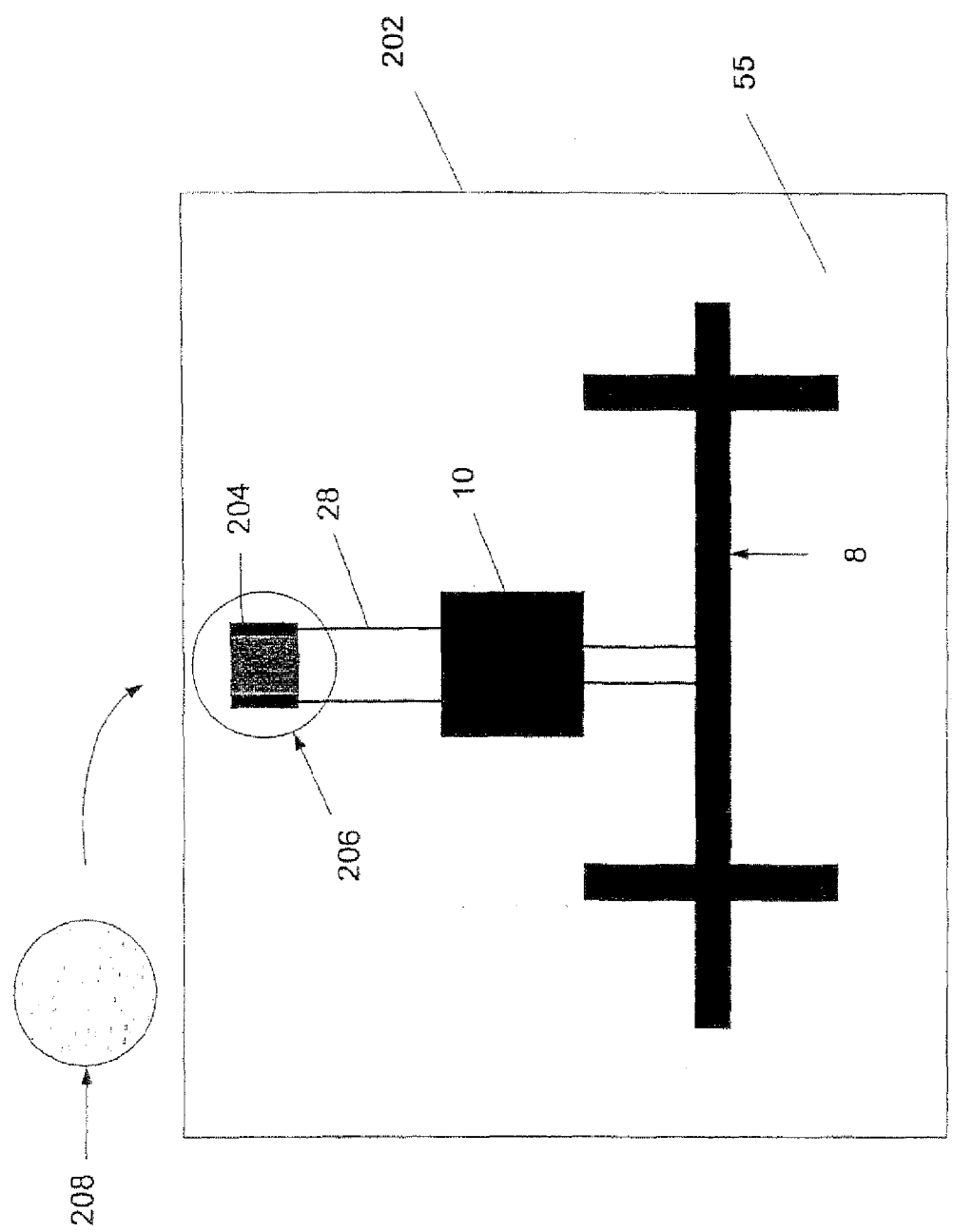
FIG. 17 depicts a generic low cost printable food-specific RFID sensor technology according to an embodiment of the present invention.

FIG. 17 shows a general printable passive RFID diagnostic food tag technology 202 that includes a sensor 204 that determines if the given food item has gone bad. The tag 202 is typically mounted in plastic and includes an RFID electronic chip 10 and an antenna 8 mounted on substrate 55. Also included are conductive leads 28. In one embodiment, all areas except sensor 204, limited by area 206, are laminated in plastic or the body of the storage unit (e.g. milk carton) to avoid shortage of the electrodes or conductive leads 28. Therefore, this sensor can be included directly into a liquid or a food surface with a high level of humidity.

A sensor cap 208 is deposited on sensor area 204. Sensor cap 208 contains a chemical that is specific to the food item and that becomes reactive only if the food turns bad. For example, the sensor tag can be included directly into meat packages on the surface of the meat itself. The RFID tag can contain all the information on the meat itself (price, date of packaging, etc.) but in this case the consumer will also be able to determine the occurrence of bacterial contamination. This is because sensor cap 208 can be made to be highly sensitive to enzymatic action by specific bacteria. If a given type of bacteria is present on the surface of the meat they will start preferentially degrading sensor cap 208. Sensor cap 208 is typically waterproof and contains a doping substance that will favor enzymatic degradation for each type of bacteria. This will allow exposure of the electrodes and will change the conductivity on the surface of sensor area 204.

The same principles can be applied to any situation with a specific chemical interaction. For example the technology can be mounted directly inside milk cartons. If milk has gone bad then its chemistry will change and the change of chemistry can be tailored to specifically react with sensor cap 208. It will be appreciated that many different sensors can be used with a single RFID chip, therefore allowing identification of specific types of bacteria. Furthermore, in another embodiment, the thickness of sensor cap 208 is varied in different sensors thereby allowing an assessment of the quantity of bacteria present. If more bacteria are present the sensor caps 208 will degrade faster and the thicker sensor caps 208 will degrade last. Therefore, this technology provides a general low cost solution for the food industry and combines electronic RFID tag labeling with very low cost sensing technology.

Figure 18:
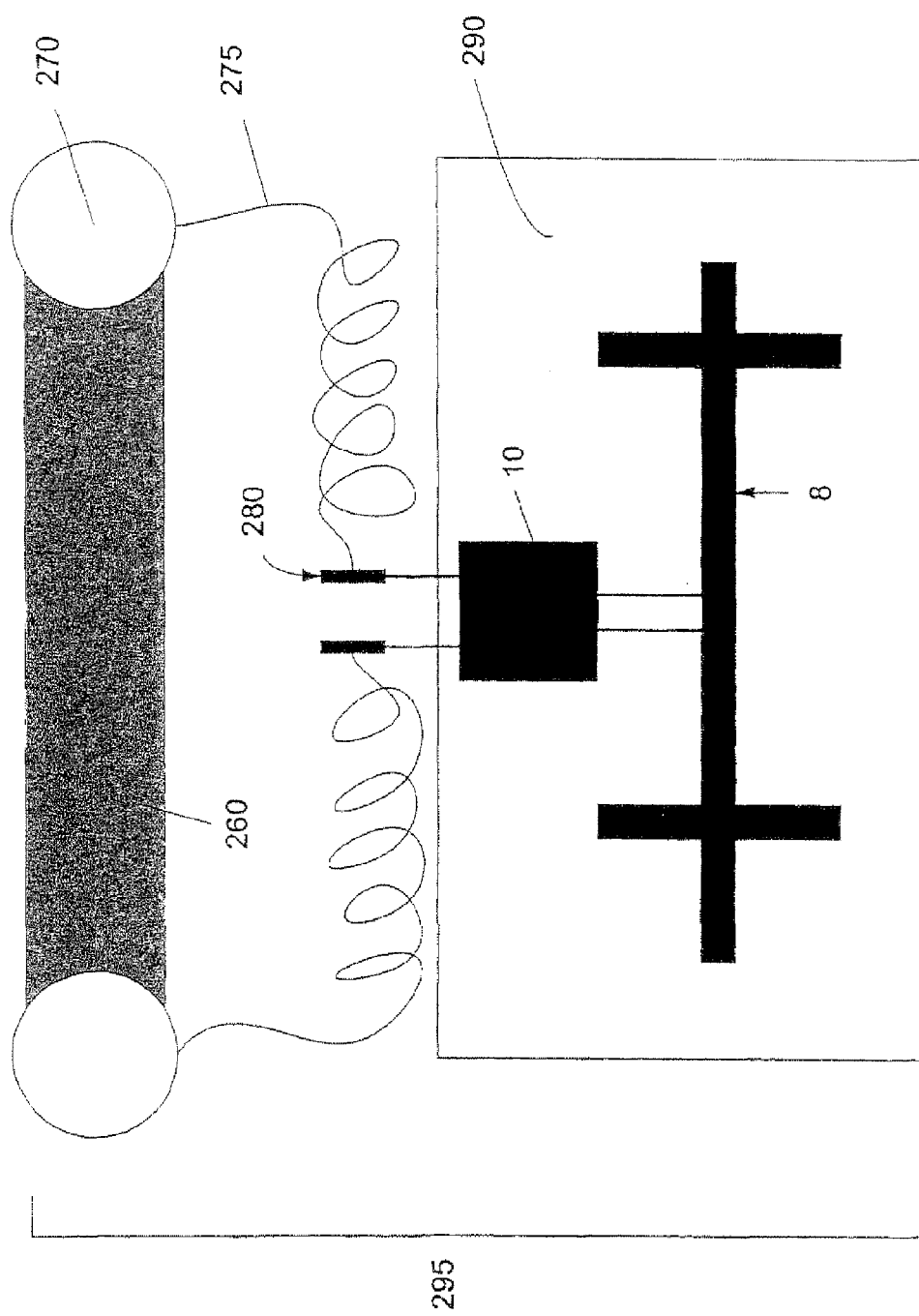
FIG. 18 depicts a RFID stress sensor according to an embodiment of the present invention.

FIG. 18 shows a diagnostic application of RFID passive sensors applied to stresses. In this embodiment, an RFID-stress sensor 295 is provided that is composed of two distinct parts. The first one forms a power and communication unit 290 that includes an RFID tag and an antenna 8. Unit 290 is connected to a sensor 260 that includes attachment points 270, typically allowing a rigid mounting, stretchable leads 275 and a connection area 280. Typically, connection area 280 is an easy "plug in" type to allow the user to easily mount the sensor onto any type of surface. Both components form a stress sensor unit 295.

The technology works as follows. Stress sensor 295 is firmly attached by a user through the use of attachment points 270. Stress sensor 295 may be attached with skews or special glues to areas where possible structural stresses may occur and need to be measured remotely. Typically sensor 260 is composed of a thin film of a material such as a flexible metal strip that may be enclosed in a thin film of plastic (not shown). Any metals that are highly conductive and that can be stretched may be used such as aluminum, gold or copper. Area 290 is not attached and therefore is not subject to the stresses. Conductivity measurements are taken periodically via a remote wireless reader such as a cell phone and stored in memory or on a remote database. Low cost wireless devices such as modified cell phones or RFID tag readers may be mounted close to the sensors and are used to periodically monitor stresses. If stresses occur, the sensor 260 will expand. Since the temperature reference is known, changes in the conductivity or resistance of the strip can be precisely measured. Because this technology is wireless and has no batteries, it is meant for long term monitoring in areas where visual access is difficult or not possible. This includes hidden structural beams in building, bridges, etc. but also any areas of high stresses (airplanes, homes, etc.). Stresses may also be monitored more dynamically with resonating MEMS structures or accelerometers as indicated in FIG. 14. A number of other methods may also be used such as compression measurement using piezoelectric materials, loss of conductivity in leads that break or snap as a result of stresses, etc. Broad market applications exist for the technology, for example insertion of a wireless RFID sensor in windows for "smart" home applications, etc.

FIGS. 19A and 19B show yet another application of the technology applied to an RFID-insect sensor such as a termite sensor. In FIG. 19A the entire sensor unit is enclosed in a unit 310 that is highly attractive to termites such as a block of wood. Unit 310 can form a "plug" of a standard size that is inserted into structural wooden supports. The unit comprises an antenna 8, an RFID electronic chip 10 and leads that are shown in more detail in FIG. 19B.

FIG. 19B shows the details of the technology in one embodiment. Conductive leads 28 are separated by a spacer 320 that is made of non-conductive material that is highly attractive to termites such as wood. If termites are present then spacer 320 will be eaten and the spacer separating electrodes or leads 28 will disappear. Electrodes 28 may be forced together by a spring (not shown). When the spacer has disappeared, the electrodes short out and therefore it is known that termites are present. In case electrodes such as shown in FIG. 19B are used a mounting power unit similar to 290 (FIG. 18) may be used. Other simple conductive methods may be used for this type of sensor.

Because this is a low cost wireless technology with no batteries, the technology can be used in hidden areas such as structural supports in houses, etc. The technology can be used to monitor remotely any type of insect damage, or may even be applied to pathogens such as bacteria using surface-specific materials that degrade only in the presence of certain enzymes.

Figure 20:
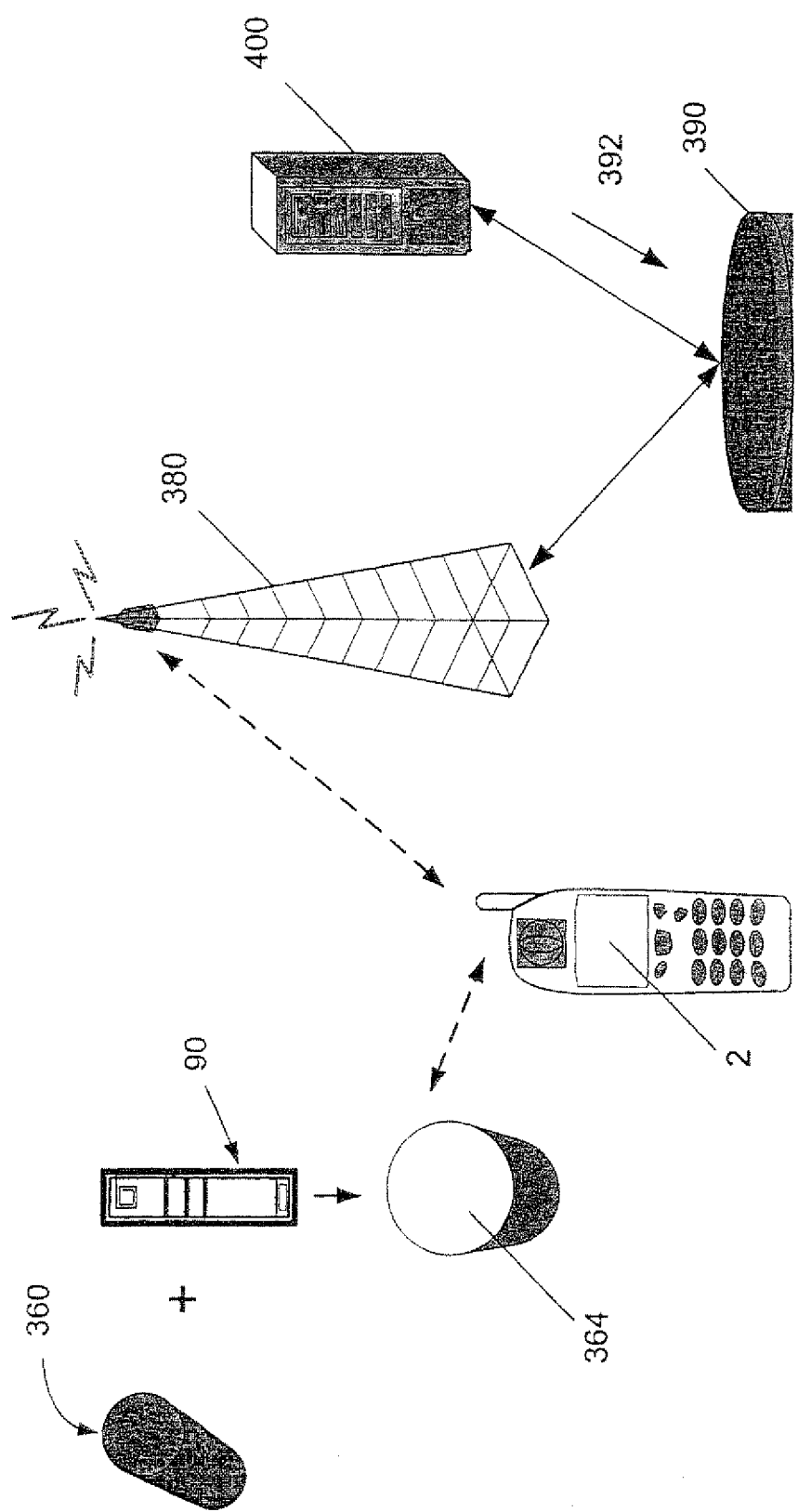
FIG. 20 shows a drug interaction test performed in a urine sample with a disposable RFID immunoassay strip according to an embodiment of the present invention.

FIG. 20 shows the uses of the technology for drug interaction testing or for general medical self-testing for any given condition. In one embodiment after drug 360 is taken a disposable wireless RFID sensor strip 90 is placed in a urine sample 364. Such strips may be provided for free with given drugs where certain toxicities may occur as a result of combination with other drugs. Using a low cost wireless device such as a cell phone 2 with RFID multi-protocol reader capability, complex drug interaction tests can be performed on-the-spot at a very low cost. This is possible by wireless access to cell phone towers 380, access to Internet 390 and to a remote storage/data processing unit 400. In one embodiment remote storage/data processing unit 400 is embodied as a computer or electronic database. Accordingly through the use of computer 400 (hereinafter remote storage/data processing unit 400 shall be referred to as computer 400), a patient can either download data to computer 400 or upload into the cell phone the necessary information to conduct any given test by matching the ID of the RFID sensor with given software and data tables stored remotely on computer 400 via link 392. In one embodiment computer 400 is a computer in a doctor's office. In another embodiment computer 400 is a drug interaction database of a pharmaceutical company. In yet another embodiment computer 400 is a computer containing reference tables for all types of RFID sensors. Since the RFID identifies each test uniquely a match of data, analyses protocols and/or software is assured. The principles described in this embodiment extend well beyond drug testing. By using disposable RFID test strips 90 with specific receptors to specific biomarkers, tests can be performed for any medical condition directly by a patient using a wireless device such as a modified cell phone. As biomarker discovery becomes more refined common wireless technologies can become used for self-diagnostics for almost anything using low cost wireless technologies such as cell phones. Such low cost diagnostic tests will be important in settings where sophisticated laboratory equipment is not available but where cell phone technology is available. The use of the technology described in this embodiment may be particularly relevant for less-developed countries where sophisticated laboratory equipment is not always available locally.

Figure 21:
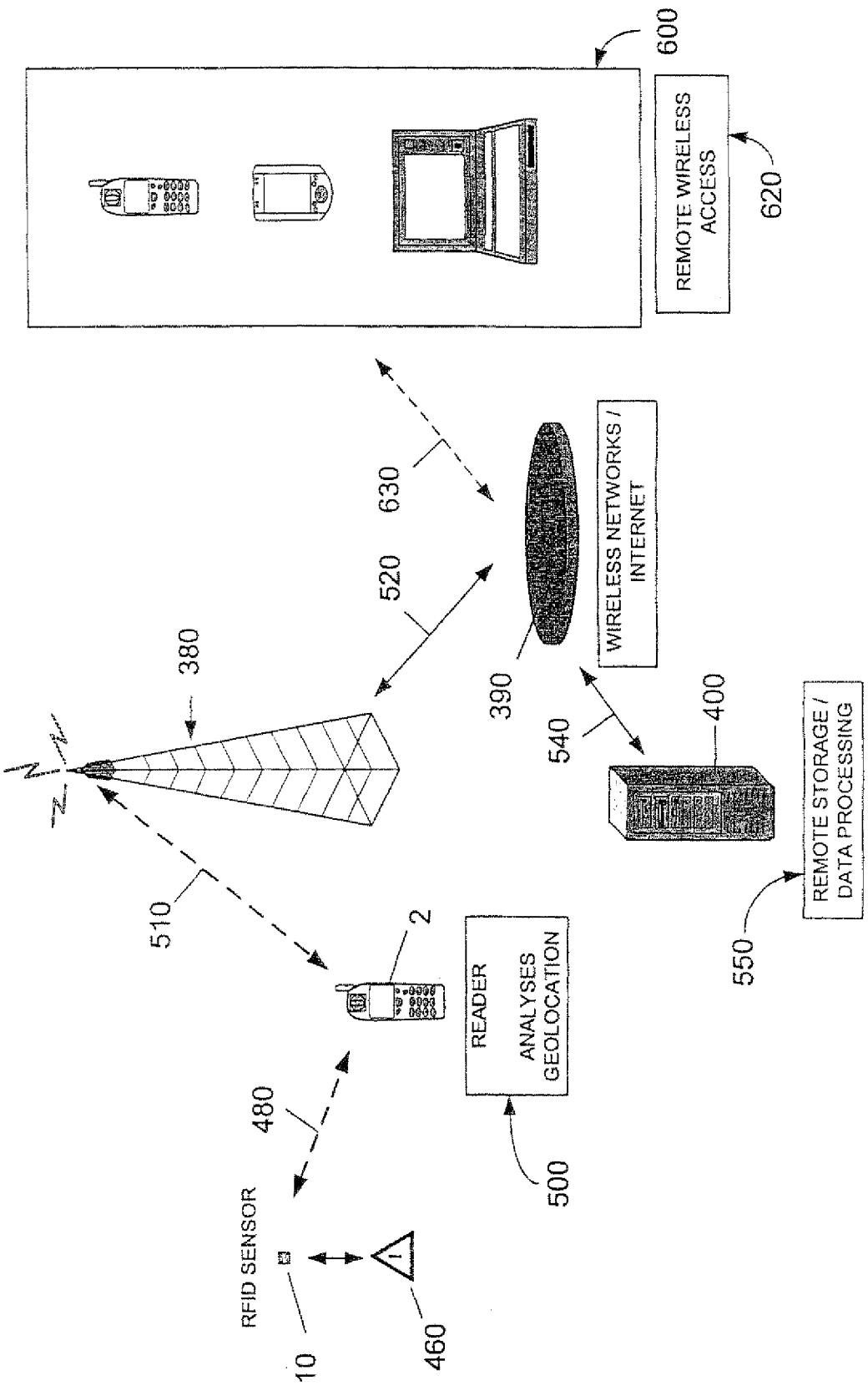
FIG. 21 shows a diagnostic passive RFID sensor network according to an embodiment of the present invention.

FIG. 21 shows the general applications of passive diagnostic RFID sensors to wireless sensor networks and wireless devices, wireless geolocation, the Internet, remote database access, remote data storage and remote data analyses. Specifically as described in this application a passive RFID diagnostic tag 10 can be used to identify any given hazard 460 in any given location. Wireless tag 10 can be activated by wireless device 2 via a wireless link 480. The microprocessor and RFID reader within wireless device 2 enable processing functions 500, which include reading, analysis and geolocation by a global positioning system (GPS) or a non-GPS means. The reading, analysis and geolocation by GPS or non-GPS means is described in U.S. Pat. No. 6,031,454 that is included herein by reference in its entirety. Wireless device 2 can communicate to a proximal cell phone tower or receiver 380 via wireless link 510 or indirectly by other existing or emerging wireless communication means such as Bluetooth. Cell phone tower 380 is linked to the Internet 390 or the wireless networks via soft or hard links 520 and to at least one remote computer 400 via soft or hard link 540. Remote computer 400 allows the functions 550, including the storage of RFID tables and associated software to analyze on the spot any given diagnostic RFID sensor tag 10. In addition using soft or hard links 630 any remote wireless device 600 may be used providing the functions 620 allowing remote access of any given RFID sensor tag via wireless device 2.

The implications of FIG. 21 are the following. Any wireless device 600 in any given geographical location can interrogate any given RFID-sensor 10 in another location. Sensor 10 may be a plurality of diagnostic sensors. For example a simple application is the following. Sensor 10 may be a temperature sensor located in a second home and include a smart sticky patch that is placed on a pipe. The owner of the home can check remotely the temperature in the home from any given location to determine for example if pipes are at risk of freezing. Two-way functionality is built into device 2. That is device 2 can be programmed to dial or send data remotely or be activated and queried at any time from any location.

Figure 22:
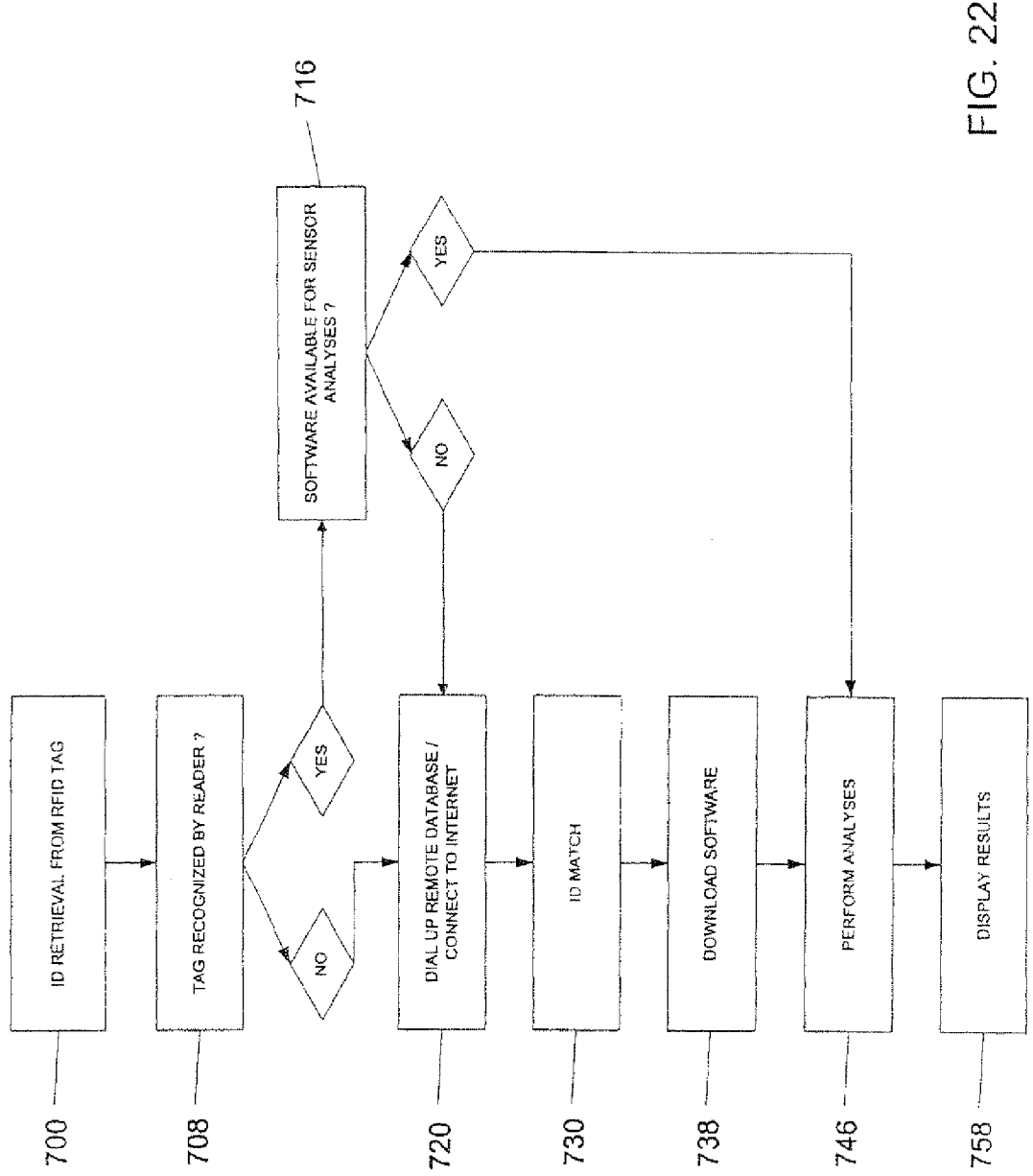
FIG. 22 shows an identification (ID) and software retrieval method that enables any RFID reader to read/interrogate any RFID tag.

FIG. 22 explains in more detail the functions in FIG. 21 and those described in this invention. Any RFID wireless reader can be used to read a compatible RFID passive sensor but a clear improvement is to use a multi-protocol reader (such as a Gen-2 enabled reader). A further improvement is to put the multi-protocol reader capability directly on a single chipset and most preferentially this chipset is the core electronic chip of a common wireless device such as a cell phone. It will be clear to those skilled in the art that the reader capability may also be integrated on a separate electronic chip that can be included in a computer as part of a plug-in smart card or even an RFID reader device connected to or built-in a Universal Serial Bus (or USB) port or similar convenient connection means. Such a device is most useful for example for a physician's office where the diagnostic functions of passive RFID diagnostic sensors described here can be fully exploited. In addition the devices described here may be compatible with Bluetooth, Zigbee or other emerging technologies, allowing further flexibility.

For consumer applications interrogation of any given RFID tag can be performed easily on a modified cell phone that includes either a special RFID read button or by pressing a series of existing keys on a keypad. Once a given tag is activated, the reader device can retrieve the ID number of the tag as shown by function 700. The reader may or may not initially recognize the tag as shown in FIG. 708. If the new international standards are adopted for RFID sensor tags then such recognition will be standard and can be integrated with either the tag itself and/or a data table in the reader 2. If the ID of the sensor tag is recognized then the reader device may or may not have the necessary software and processing ability to analyze said sensor as shown in 716. If the software is available then the analysis can be completed immediately as shown in 746. However if the software is not available then the device must first obtain it from a given remote database 400 via function 720. This may be a centralized database for RFID tags or a diagnostics database that is accessed only by paying an access fee. Subsequently, the ID of the RFID sensor is matched to a given class of sensor (e.g. a glucose sensor) and the software and/or instructions for the analyses are downloaded into the reader 2 as shown in function 738. The device is then equipped to perform the analysis 746. Additional communication with computer 400 may occur if the analyses are complex (e.g. neural net or multivariate) and exceed the processing capabilities of the reader. Results are subsequently displayed on the cell phone or reader as shown in 758. Alternatively results may be displayed or stored remotely (e.g. in a doctor's office, etc.). The pathway described above is not limited to passive RFID diagnostic sensors. It can also include EPC tags, other RF tags or sensors such as Bluetooth and other wireless functions such as smart shopping or "smart wallet".

Figure 23:
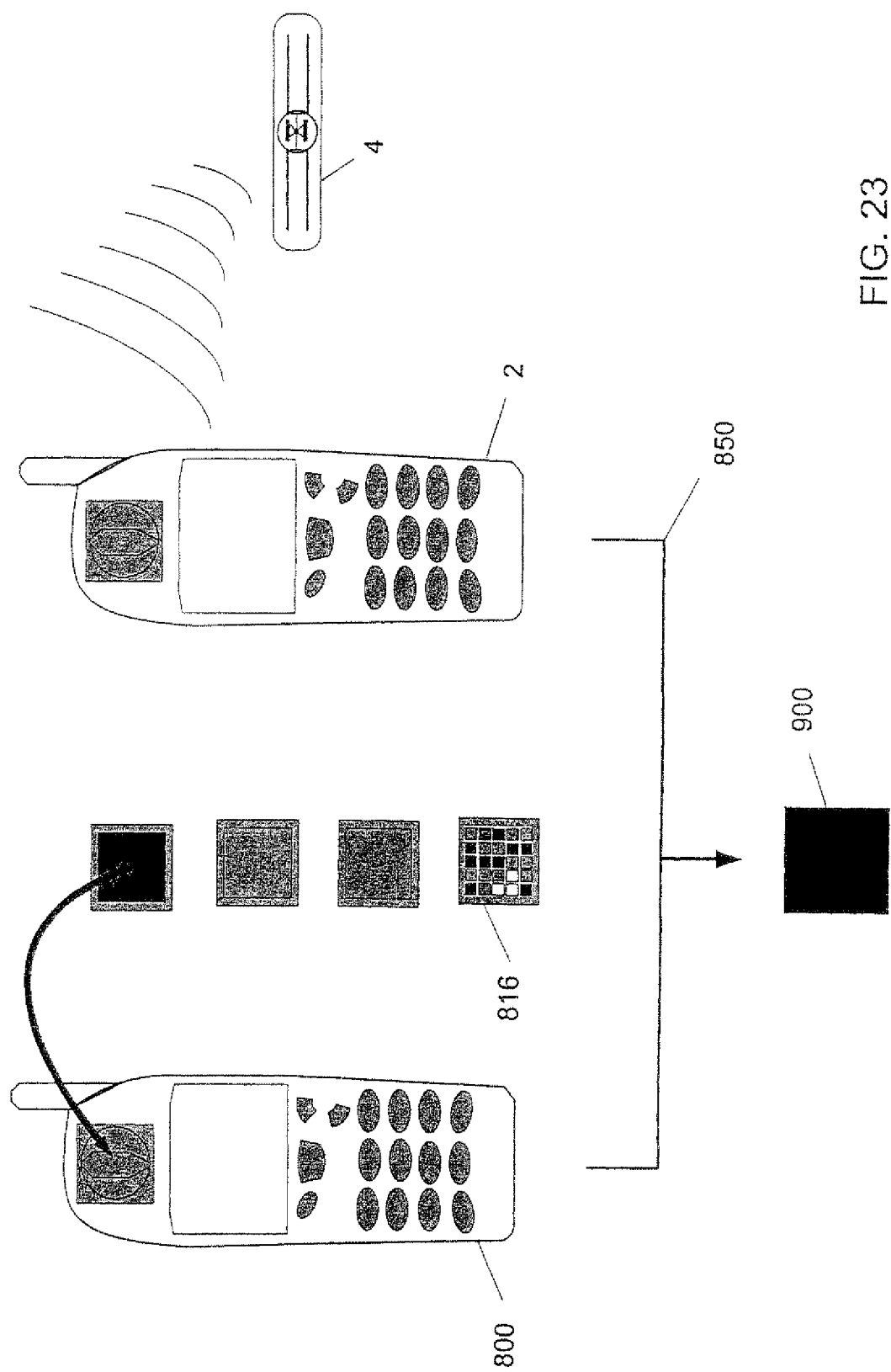
FIG. 23 shows the integration of both passive and active sensor reader capabilities onto a single wireless chipset.

FIG. 23 shows the integration of the two types of sensor reader functions into a single wireless reader and a resulting new type of wireless chipset that can be included into any wireless reader. Starting with device 800 and as explained in U.S. Pat. No. 6,031,454 and U.S. Patent Publication No. 2004/0119591 A1 by the present inventor that are incorporated by reference in their entirety, a wireless device such as a cell phone may be modified to accommodate any number of sensors 816, including diagnostic sensors. These are typically "active" sensors since they are directly connected to the wireless device itself. An example of this is a cell phone that is also a person-specific asthma detector as described in U.S. Patent Publication No. 2004/0119591 A1. In addition to this capability, any wireless device 2 such as a cell phone may also be modified to interrogate remotely any active or passive wireless sensor 4 as described in this application. This capability most preferentially is a multi-protocol capability and includes emerging standards such as Gen-2, other future international standards for RFID and Bluetooth.

The cell phone may already have other multi-functionality integrated therein (such as Internet access). A widely adopted emerging standard is referred to as Third Generation or 3G functionality that is included directly into the chipset.

In this invention the ability to read any "plug-in" sensor and any remote wireless sensor are combined in 850 and results in a new multi-function chipset that allows any wireless device to read any sensor, whether a "plug-in" sensor or a remote wireless sensor. Most preferentially these capabilities are included into the core wireless electronic chip (such as the 3G chip), thereby extending the capabilities of the wireless device to read and analyze instantly any type of sensor, RFID tag, RFID sensor tag or Bluetooth sensor, regardless of the manufacturer, location or nature of the sensor.

As described in the above embodiments, wireless passive RFID sensors can be used for many different types of diagnostic applications in the consumer markets, defense and Homeland Security, building security industry, medical diagnostics industry, food safety industry, and for home safety and other applications using a common wireless device such as a modified cell phone. This technology provides great convenience to consumers, to workers or to any person concerned with the detection of external threats or having special medical needs or concerns.

The diagnostic sensor technologies described here can also be adapted to networks and to national emergencies, where tagged items can be read remotely (thousands of feet), by employing special high power readers.

While various embodiments of the present invention have been described above, it should be understood that they have been presented by way of example only, and not limitation. It will be apparent to persons skilled in the relevant art that various changes in faun and detail can be made therein without departing from the spirit and scope of the invention. Thus, the breadth and scope of the present invention should not be limited by any of the above-described embodiments, but should be defined only in accordance with the following claims and their equivalents.

What is claimed is:

1. An immunoassay test strip system for use in conducting quantitative immunoassay diagnostic measurements comprising:
   an immunoassay test strip including a substrate; at least one test area located on said substrate for capturing antigens that flow through the immunoassay test strip;
   a radio frequency identification (RFID) tag and a sensor module combination electronically connected to each other and integrated with said substrate; said sensor module capable of quantitatively detecting captured antigens on said test area and said RFID tag and sensor module combination being capable of generating and transmitting at least one signal that includes information regarding the quantity of said antigen captured on said test area and identification of the RFID tag and sensor module combination;
   a wireless reader adapted to communicate wirelessly with said RFID tag and sensor module combination through the use of multiple protocols to receive said at least one signal that corresponds to the quantity of antigens captured by said at least one test area; and
   said wireless reader further adapted to communicate wirelessly over a network through the use of multiple communication protocols to download software wirelessly from a remote location based on the identification of the RFID tag and sensor module combination to enable reading and analysis by said wireless reader of the at least one signal received from said RFID tag and sensor module combination.

2. An immunoassay test strip system as set forth in claim 1 wherein said wireless reader is a cellular telephone.

3. An immunoassay test strip system as set forth in claim 1 wherein said test strip is disposable.

4. An immunoassay test strip system of claim 1 wherein said test strip is adapted to perform quantitative protein measurements.

5. An immunoassay test strip system of claim 1 wherein said test strip is adapted to perform quantitative biomarker measurements.

6. An immunoassay test strip system of claim 1 wherein said test strip forms a disease-specific sensor device.

7. An immunoassay test strip system of claim 1 wherein said test strip is adapted to perform pre-disease specific tests.

8. An immunoassay test strip system of claim 1 wherein said test strip is adapted to perform drug toxicity tests.

9. An immunoassay test strip system of claim 1 wherein the immunoassay test strip includes an integrated radio frequency chip that is communicative with the wireless device and that provides power to said test area.

10. An immunoassay test strip system of claim 1 wherein said radio-frequency chip is selected from the group consisting of an RFID chip and a Bluetooth chip and a Zigbee chip and an IEEE 1073 chip.

11. An immunoassay test strip system of claim 9 wherein said test area is an electro-immunoassay for measuring the presence and a quantity of a biological material.

12. An immunoassay test strip system of claim 1 wherein said wireless reader is a PDA.

13. An immunoassay test strip system of claim 1 wherein the multiple communication protocols comprises one or more of Bluetooth, Wi-Fi, Broadband, WLAN, or 3G communication protocols.

* * * * *

UNITED STATES PATENT AND TRADEMARK OFFICE
CERTIFICATE OF CORRECTION

PATENT NO. : 9,041,538 B2  
APPLICATION NO. : 13/108643  
DATED : May 26, 2015  
INVENTOR(S) : John P. Peeters Page 1 of 1

It is certified that error appears in the above-identified patent and that said Letters Patent is hereby corrected as shown below:

In the specification,

Column 13, Line 45 "ease" should be --case--.

Signed and Sealed this
Twenty-second Day of March, 2016

Michelle K. Lee
*Director of the United States Patent and Trademark Office*